US011873335B2

(12) United States Patent
Wang et al.

(10) Patent No.: US 11,873,335 B2
(45) Date of Patent: Jan. 16, 2024

(54) ANTI-FOLATE RECEPTOR 1 ANTIBODIES AND USES THEREOF

(71) Applicant: Phanes Therapeutics, Inc., San Diego, CA (US)

(72) Inventors: Minghan Wang, San Diego, CA (US); Hui Zou, Dallas, TX (US); Haiqun Jia, San Diego, CA (US)

(73) Assignee: Phanes Therapeutics, Inc., San Diego, CA (US)

( * ) Notice: Subject to any disclaimer, the term of this patent is extended or adjusted under 35 U.S.C. 154(b) by 744 days.

(21) Appl. No.: 15/733,541

(22) PCT Filed: Mar. 7, 2019

(86) PCT No.: PCT/US2019/021084
§ 371 (c)(1),
(2) Date: Aug. 24, 2020

(87) PCT Pub. No.: WO2019/177854
PCT Pub. Date: Sep. 19, 2019

(65) Prior Publication Data
US 2021/0002363 A1 Jan. 7, 2021

Related U.S. Application Data

(60) Provisional application No. 62/642,213, filed on Mar. 13, 2018.

(51) Int. Cl.
| | | |
|---|---|---|
| *C07K 16/28* | (2006.01) | |
| *G01N 33/574* | (2006.01) | |
| *A61K 39/395* | (2006.01) | |
| *A61K 39/00* | (2006.01) | |
| *A61P 35/00* | (2006.01) | |
| *G01N 33/577* | (2006.01) | |

(52) U.S. Cl.
CPC ....... *C07K 16/28* (2013.01); *G01N 33/57492* (2013.01); *A61K 39/395* (2013.01); *A61K 2039/505* (2013.01); *A61P 35/00* (2018.01); *C07K 2317/24* (2013.01); *C07K 2317/31* (2013.01); *C07K 2317/56* (2013.01); *C07K 2317/565* (2013.01); *C07K 2317/732* (2013.01); *C07K 2317/92* (2013.01); *G01N 33/574* (2013.01); *G01N 33/577* (2013.01); *G01N 2333/705* (2013.01)

(58) Field of Classification Search
CPC .......................... C07K 16/28; C07K 2317/24; C07K 2317/31; C07K 2317/56; C07K 2317/565; C07K 2317/732; C07K 2317/92; G01N 33/574; G01N 33/57492; G01N 33/577; G01N 2333/705; A61P 35/00; A61K 39/395; A61K 2039/505
See application file for complete search history.

(56) References Cited

U.S. PATENT DOCUMENTS

| | | | | |
|---|---|---|---|---|
| 9,200,073 B2 * | 12/2015 | Carrigan | .......... | G01N 33/57492 |
| 2010/0150902 A1 | 6/2010 | Haeuw | | |
| 2011/0171213 A1 | 7/2011 | Houhou | | |
| 2014/0205610 A1 | 7/2014 | Ando | | |
| 2016/0083471 A1 | 3/2016 | Ab | | |
| 2018/0044424 A1 | 2/2018 | June | | |

FOREIGN PATENT DOCUMENTS

| | | |
|---|---|---|
| WO | 2005080431 | 9/2005 |
| WO | 2006116592 | 11/2006 |
| WO | 2008031577 | 3/2008 |
| WO | 2008145136 | 12/2008 |
| WO | 2011106528 | 9/2011 |
| WO | 2012054654 | 4/2012 |
| WO | 2012061759 | 5/2012 |
| WO | 2012099973 | 7/2012 |
| WO | 2012135675 | 10/2012 |
| WO | 2013012722 | 1/2013 |
| WO | 2013172951 | 11/2013 |
| WO | 2014036495 | 3/2014 |
| WO | 2014055771 | 4/2014 |
| WO | 2014087863 | 6/2014 |
| WO | 2014104270 | 7/2014 |
| WO | 2014144722 | 9/2014 |
| WO | 2014186403 | 11/2014 |
| WO | 2014205342 | 12/2014 |
| WO | 2015031815 | 3/2015 |
| WO | 2015054400 | 4/2015 |
| WO | 2015085003 | 6/2015 |
| WO | 2015196167 | 12/2015 |
| WO | 2016036794 | 3/2016 |
| WO | 2016079050 | 5/2016 |
| WO | 2016079076 | 5/2016 |

(Continued)

OTHER PUBLICATIONS

International Preliminary Report on Patentability for PCT/US2019/021084, dated Sep. 15, 2020, 7 pages.
International Search Report and Written Opinion for PCT/US2019/021084, dated Jul. 24, 2019, 11 pages.
Salazar et al., "The folate receptor: What does it promise in tissue-targeted therapeutics?" Cancer Metastasis Rev 2007; 26:141-52.
Toffoli et al., "Overexpression of folate binding protein in ovarian cancers", Int J Cancer 1997; 74:193-198.
Boogerd et al., "Concordance of folate receptor-a expression between biopsy, primary tumor and metastasis in breast cancer and lung cancer patients", Oncotarget 2016; 7:17442-17454.
Weitman et al., "Distribution of the Folate Receptor GP38 in Normal and Malignant Cell Lines and Tissues", Cancer Res 1992; 52:3396-3401.

(Continued)

*Primary Examiner* — Hong Sang
(74) *Attorney, Agent, or Firm* — Ice Miller LLP

(57) ABSTRACT

Anti-FOLR1 antibodies and antigen-binding fragments thereof are described. Also described are nucleic acids encoding the antibodies, compositions comprising the antibodies, methods of producing the antibodies, and methods of using the antibodies for treating or preventing diseases, such as cancer.

13 Claims, 11 Drawing Sheets

Specification includes a Sequence Listing.

(56) References Cited

FOREIGN PATENT DOCUMENTS

| WO | 2016126608 | 8/2016 |
| WO | 2016168440 | 10/2016 |
| WO | 2017049149 | 3/2017 |
| WO | 2018071597 | 4/2018 |
| WO | 2018098277 | 5/2018 |
| WO | 2018213260 | 11/2018 |

OTHER PUBLICATIONS

Cheung et al., "Targeting folate receptor alpha for cancer treatment", Oncotarget 2016; 7:52553-52574.

* cited by examiner

SEQUENCE LISTING

<160> NUMBER OF SEQ ID NOS: 135

<210> SEQ ID NO 1
<211> LENGTH: 117
<212> TYPE: PRT
<213> ORGANISM: Artificial Sequence
<220> FEATURE:
<223> OTHER INFORMATION: F4 Heavy Chain Variable Region

<400> SEQUENCE: 1

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

```
Gly Met His Trp Val Arg Gln Ala Pro Glu Lys Gly Leu Glu Trp Val
        35                  40                  45

Ala Phe Ile Ser Ser Gly Ser Asn Thr Ile Tyr Tyr Ala Asp Ile Val
 50                  55                  60

Lys Gly Arg Phe Ala Ile Ser Arg Asp Asn Ala Lys Asn Thr Leu Phe
 65                  70                  75                  80

Leu Gln Met Ala Ser Leu Arg Ser Glu Asp Thr Ala Leu Tyr Tyr Cys
                 85                  90                  95

Ala Arg Leu Ala Glu Trp Asp Val Ala Tyr Trp Gly Gln Gly Thr Leu
            100                 105                 110

Val Thr Val Ser Ala
        115

<210> SEQ ID NO 2
<211> LENGTH: 108
<212> TYPE: PRT
<213> ORGANISM: Artificial Sequence
<220> FEATURE:
<223> OTHER INFORMATION: F4 Light Chain Variable Region

<400> SEQUENCE: 2

Asp Ile Val Leu Thr Gln Ser Pro Ala Thr Leu Ser Val Thr Pro Gly
 1               5                  10                  15

Asp Arg Ile Ser Leu Ser Cys Arg Ala Ser Gln Asn Ile Asn Asn Asn
                 20                  25                  30

Leu His Trp Tyr Gln Gln Lys Ser His Glu Ser Pro Arg Leu Leu Ile
             35                  40                  45

Lys Phe Ala Ser Gln Ser Ile Ser Gly Ile Pro Ser Arg Phe Ser Gly
 50                  55                  60

Ser Gly Ser Gly Thr Asp Phe Thr Leu Asn Ile Asn Gly Val Glu Thr
 65                  70                  75                  80

Glu Asp Phe Gly Met Tyr Phe Cys Gln Gln Ile Tyr Ser Trp Pro Gln
                 85                  90                  95

Leu Thr Phe Gly Ala Gly Thr Arg Leu Glu Leu Lys
            100                 105

<210> SEQ ID NO 3
<211> LENGTH: 118
<212> TYPE: PRT
<213> ORGANISM: Artificial Sequence
<220> FEATURE:
<223> OTHER INFORMATION: F5 Heavy Chain Variable Region

<400> SEQUENCE: 3

Glu Val Gln Leu Val Glu Ser Gly Gly Glu Leu Val Lys Pro Gly Gly
 1               5                  10                  15

Ser Leu Lys Leu Ser Cys Ala Val Ser Gly Phe Thr Phe Ser Asn Tyr
                 20                  25                  30

Gly Met Ser Trp Val Arg Gln Thr Pro Asp Lys Arg Leu Glu Trp Val
            35                  40                  45

Ala Thr Ile Ser Ser Gly Gly Ser Tyr Thr Tyr Tyr Pro Asp Ser Val
 50                  55                  60

Lys Gly Arg Phe Thr Ile Ser Arg Asp Asn Asp Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ser Thr Gln Gly Ser Ser Gly Tyr Val Gly Tyr Trp Gly Gln Gly Thr
            100                 105                 110
```

Thr Leu Thr Val Ser Ser
        115

<210> SEQ ID NO 4
<211> LENGTH: 106
<212> TYPE: PRT
<213> ORGANISM: Artificial Sequence
<220> FEATURE:
<223> OTHER INFORMATION: F5 Light Chain Variable Region

<400> SEQUENCE: 4

Asp Ile Gln Met Thr Gln Ser Pro Ser Leu Ser Ala Phe Leu Gly
1               5                   10                  15

Gly Lys Val Thr Ile Thr Cys Lys Ala Ser Gln Asp Ile Thr Asn Phe
            20                  25                  30

Ile Gly Trp Tyr Gln His Lys Pro Gly Lys Pro Arg Leu Leu Ile
            35                  40                  45

Ser Tyr Thr Ser Ile Leu Glu Ser Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Tyr Asn Leu Trp Thr
                85                  90                  95

Phe Gly Gly Gly Thr Lys Leu Glu Ile Lys
            100                 105

<210> SEQ ID NO 5
<211> LENGTH: 118
<212> TYPE: PRT
<213> ORGANISM: Artificial Sequence
<220> FEATURE:
<223> OTHER INFORMATION: F7 Heavy Chain Variable Region

<400> SEQUENCE: 5

Glu Phe Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Asn Met Asn Trp Val Lys Gln Ser Asn Gly Lys Ser Leu Glu Trp Ile
            35                  40                  45

Gly Val Ile Asp Pro Asn Tyr Gly Thr Thr Asn Tyr Asn Gln Lys Phe
    50                  55                  60

Val Gly Lys Ala Thr Leu Thr Val Asp Gln Ser Ser Ile Thr Ala Tyr
65                  70                  75                  80

Met Gln Leu Asn Ser Leu Thr Ala Glu Asp Ser Ala Val Tyr Phe Cys
                85                  90                  95

Ala Ile Lys Gly Tyr Gly Asn Pro Ala Ala Tyr Trp Gly Gln Gly Thr
            100                 105                 110

Leu Val Thr Val Ser Ala
        115

<210> SEQ ID NO 6
<211> LENGTH: 106
<212> TYPE: PRT
<213> ORGANISM: Artificial Sequence
<220> FEATURE:
<223> OTHER INFORMATION: F7 Light Chain Variable Region

<400> SEQUENCE: 6

```
Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Leu Ala Trp Tyr Gln His Glu Pro Gly Lys Gly Pro Arg Leu Leu Ile
        35                  40                  45

Arg Tyr Thr Ser Ile Leu Glu Ser Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Tyr Asn Leu Trp Thr
                85                  90                  95

Phe Gly Gly Gly Thr Lys Leu Glu Ile Lys
            100                 105
```

<210> SEQ ID NO 7
<211> LENGTH: 121
<212> TYPE: PRT
<213> ORGANISM: Artificial Sequence
<220> FEATURE:
<223> OTHER INFORMATION: F8 Heavy Chain Variable Region

<400> SEQUENCE: 7

```
Glu Val Met Leu Val Glu Ser Gly Gly Leu Val Lys Pro Gly Gly
1               5                   10                  15

Ser Leu Lys Leu Ser Cys Val Ala Ser Gly Phe Thr Leu Ser Thr Tyr
            20                  25                  30

Ala Met Ser Trp Val Arg Gln Thr Pro Glu Lys Arg Leu Glu Trp Val
        35                  40                  45

Ala Thr Ile Ser Gly Gly Gly Asp Thr Tyr His Leu Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg Gln Ser His Tyr Gly Ser Tyr Tyr Phe Asp Asn Trp Gly
            100                 105                 110

Gln Gly Thr Thr Leu Thr Val Ser Ser
        115                 120
```

<210> SEQ ID NO 8
<211> LENGTH: 107
<212> TYPE: PRT
<213> ORGANISM: Artificial Sequence
<220> FEATURE:
<223> OTHER INFORMATION: F8 Light Chain Variable Region

<400> SEQUENCE: 8

```
Asp Ile Gln Met Thr Gln Ser Pro Ala Ser Leu Ser Ala Ser Val Gly
1               5                   10                  15

Glu Ile Val Thr Ile Ile Cys Arg Val Ser Glu Asn Ile Asp Ser Tyr
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Ser Gln Tyr Ser Leu Lys Ile Asn Ser Leu Gln Ser
65                  70                  75                  80
```

Glu Asp Val Ala Arg Tyr Tyr Cys Gln His Tyr Tyr Thr Thr Pro Pro
                85                  90                  95

Thr Phe Gly Gly Gly Thr Lys Leu Asp Ile Lys
            100                 105

<210> SEQ ID NO 9
<211> LENGTH: 120
<212> TYPE: PRT
<213> ORGANISM: Artificial Sequence
<220> FEATURE:
<223> OTHER INFORMATION: F10 Heavy Chain Variable Region

<400> SEQUENCE: 9

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Arg Gln Arg Pro Gly Lys Gly Leu Glu Trp Ile
        35                  40                  45

Gly Arg Ile Tyr Pro Gly Asp Gly Tyr Thr His Tyr Asn Gly Met Phe
    50                  55                  60

Lys Gly Lys Ala Thr Leu Thr Ala Asp Lys Ser Ser Ser Thr Gly Tyr
65                  70                  75                  80

Met Gln Leu Ser Ser Leu Thr Ser Glu Asp Ser Ala Val Tyr Phe Cys
                85                  90                  95

Thr Arg His Gly Asp Phe Pro Tyr Trp Tyr Phe Asp Val Trp Gly Thr
            100                 105                 110

Gly Thr Thr Val Thr Val Ser Ser
        115                 120

<210> SEQ ID NO 10
<211> LENGTH: 107
<212> TYPE: PRT
<213> ORGANISM: Artificial Sequence
<220> FEATURE:
<223> OTHER INFORMATION: F10 Light Chain Variable Region

<400> SEQUENCE: 10

Asp Ile Gln Met Thr Gln Ser Pro Ala Ser Leu Ser Ala Ser Val Gly
1               5                   10                  15

Glu Ser Val Thr Ile Thr Cys Arg Ala Ser Glu Asn Ile Asp Ser Tyr
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Val Gly Val Pro Ser Arg Phe Ser Gly
    50                  55                  60

Ser Gly Ser Gly Thr Gln Tyr Thr Leu Lys Ile Asn Ser Leu Gln Ser
65                  70                  75                  80

Glu Asp Val Ala Arg Tyr Tyr Cys Gln His His Tyr Ser Thr Pro Pro
                85                  90                  95

Thr Phe Gly Gly Gly Thr Lys Leu Glu Ile Lys
            100                 105

<210> SEQ ID NO 11
<211> LENGTH: 117
<212> TYPE: PRT
<213> ORGANISM: Artificial Sequence
<220> FEATURE:
<223> OTHER INFORMATION: F17 Heavy Chain Variable Region

<400> SEQUENCE: 11

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Asp Phe
            20                  25                  30

Gly Met His Trp Ile Arg Gln Ala Pro Glu Arg Gly Leu Glu Trp Val
        35                  40                  45

Ala Tyr Met Ser Tyr Thr Pro Gly Thr Phe His Tyr Ala Asp Thr Val
    50                  55                  60

Lys Asp Arg Phe Phe Ile Ser Arg Asp Asn Ala Lys Asn Thr Leu Phe
65                  70                  75                  80

Leu Gln Met Thr Ser Leu Arg Ser Asp Asp Thr Ala Met Tyr Tyr Cys
                85                  90                  95

Ala Arg Val His Val Gly Thr Val Asp Tyr Trp Gly Gln Gly Thr Ser
            100                 105                 110

Val Thr Val Ser Ser
        115

<210> SEQ ID NO 12
<211> LENGTH: 108
<212> TYPE: PRT
<213> ORGANISM: Artificial Sequence
<220> FEATURE:
<223> OTHER INFORMATION: F17 Light Chain Variable Region

<400> SEQUENCE: 12

Asp Val Val Leu Thr Gln Ser Pro Ala Thr Leu Ser Val Thr Pro Gly
1               5                   10                  15

Asp Ser Val Ser Leu Ser Cys Arg Ala Ser Gln Asn Ile Asn Asn Asn
            20                  25                  30

Leu His Trp Phe Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Asn Val Glu Thr
65                  70                  75                  80

Glu Asp Phe Gly Ile Tyr Phe Cys Gln Gln Ser Asn Ser Trp Pro Ala
                85                  90                  95

Leu Thr Phe Gly Thr Gly Thr Lys Val Glu Leu Lys
            100                 105

<210> SEQ ID NO 13
<211> LENGTH: 121
<212> TYPE: PRT
<213> ORGANISM: Artificial Sequence
<220> FEATURE:
<223> OTHER INFORMATION: F19 Heavy Chain Variable Region

<400> SEQUENCE: 13

Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Asp Lys Gly Leu Glu Trp Val
        35                  40                  45

Ala Gln Ile Gly Asn Lys Phe His Asn Tyr Glu Thr Tyr Tyr Ser Asp
    50                  55                  60

```
Ser Val Lys Gly Arg Phe Thr Ile Ser Arg Asp Asp Ser Lys Ser Ser
 65                  70                  75                  80

Val Tyr Leu Gln Met Asn Ser Leu Arg Val Glu Asp Thr Gly Ile Tyr
                 85                  90                  95

Tyr Cys Thr Lys Leu Gly Arg Gly Tyr Tyr Val Met Asp Tyr Trp Gly
            100                 105                 110

Gln Gly Thr Ser Val Thr Val Ser Ser
            115                 120
```

<210> SEQ ID NO 14
<211> LENGTH: 107
<212> TYPE: PRT
<213> ORGANISM: Artificial Sequence
<220> FEATURE:
<223> OTHER INFORMATION: F19 Light Chain Variable Region

<400> SEQUENCE: 14

```
Asp Ile Gln Met Thr Gln Thr Thr Ser Ser Leu Ser Ala Ser Leu Gly
  1               5                  10                  15

Asp Arg Val Thr Leu Asn Cys Arg Ala Ser Gln Asp Ile Thr Asn His
             20                  25                  30

Leu Asn Trp Phe Gln Gln Lys Pro Asp Gly Thr Phe Gln Leu Leu Ile
         35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Phe Ala Thr Tyr Phe Cys Gln Gln Asp Ser Gln His Pro Trp
                 85                  90                  95

Thr Phe Gly Gly Gly Thr Lys Leu Glu Ile Lys
            100                 105
```

<210> SEQ ID NO 15
<211> LENGTH: 121
<212> TYPE: PRT
<213> ORGANISM: Artificial Sequence
<220> FEATURE:
<223> OTHER INFORMATION: F20 Heavy Chain Variable Region

<400> SEQUENCE: 15

```
Gln Val Gln Leu Gln Gln Ser Gly Ala Glu Leu Val Lys Pro Gly Ala
  1               5                  10                  15

Ser Val Lys Leu Ser Cys Lys Ala Ser Gly Tyr Thr Phe Ala Ser Tyr
             20                  25                  30

Tyr Leu Tyr Trp Val Lys Gln Arg Pro Gly Gln Gly Leu Glu Trp Ile
         35                  40                  45

Gly Glu Ile Asn Pro Arg Ser Gly Gly Thr Asn Phe Asn Glu Lys Phe
 50                  55                  60

Lys Ser Lys Ala Thr Val Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ser Arg Ser Gly Arg Leu Arg Gly Phe Tyr Thr Met Asp Tyr Trp Gly
            100                 105                 110

Gln Gly Thr Ser Val Thr Val Ser Ser
            115                 120
```

<210> SEQ ID NO 16
<211> LENGTH: 106
<212> TYPE: PRT
<213> ORGANISM: Artificial Sequence
<220> FEATURE:
<223> OTHER INFORMATION: F20 Light Chain Variable Region

<400> SEQUENCE: 16

Asn Ile Val Met Thr Gln Ser Pro Lys Ser Met Ser Val Ser Val Gly
1               5                   10                  15

Glu Arg Val Thr Leu Ser Cys Lys Ala Gly Glu Asn Val Gly Ser Tyr
            20                  25                  30

Val Ser Trp Tyr Gln Gln Lys Pro Glu Gln Ser Pro Glu Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr Tyr Cys Gly Gln Thr Tyr Arg Phe Leu Thr
                85                  90                  95

Phe Gly Ala Gly Thr Lys Leu Glu Leu Lys
            100                 105

<210> SEQ ID NO 17
<211> LENGTH: 8
<212> TYPE: PRT
<213> ORGANISM: Artificial Sequence
<220> FEATURE:
<223> OTHER INFORMATION: F4 HCDR1

<400> SEQUENCE: 17

Gly Phe Thr Phe Ser Asp Tyr Gly
1               5

<210> SEQ ID NO 18
<211> LENGTH: 8
<212> TYPE: PRT
<213> ORGANISM: Artificial Sequence
<220> FEATURE:
<223> OTHER INFORMATION: F4 HCDR2

<400> SEQUENCE: 18

Ile Ser Ser Gly Ser Asn Thr Ile
1               5

<210> SEQ ID NO 19
<211> LENGTH: 10
<212> TYPE: PRT
<213> ORGANISM: Artificial Sequence
<220> FEATURE:
<223> OTHER INFORMATION: F4 HCDR3

<400> SEQUENCE: 19

Ala Arg Leu Ala Glu Trp Asp Val Ala Tyr
1               5                   10

<210> SEQ ID NO 20
<211> LENGTH: 8
<212> TYPE: PRT
<213> ORGANISM: Artificial Sequence
<220> FEATURE:
<223> OTHER INFORMATION: F5 HCDR1

<400> SEQUENCE: 20

Gly Phe Thr Phe Ser Asn Tyr Gly
1               5

<210> SEQ ID NO 21
<211> LENGTH: 8
<212> TYPE: PRT
<213> ORGANISM: Artificial Sequence
<220> FEATURE:
<223> OTHER INFORMATION: F5 HCDR2

<400> SEQUENCE: 21

Ile Ser Ser Gly Gly Ser Tyr Thr
1               5

<210> SEQ ID NO 22
<211> LENGTH: 11
<212> TYPE: PRT
<213> ORGANISM: Artificial Sequence
<220> FEATURE:
<223> OTHER INFORMATION: F5 HCDR3

<400> SEQUENCE: 22

Ser Thr Gln Gly Ser Ser Gly Tyr Val Gly Tyr
1               5                   10

<210> SEQ ID NO 23
<211> LENGTH: 8
<212> TYPE: PRT
<213> ORGANISM: Artificial Sequence
<220> FEATURE:
<223> OTHER INFORMATION: F7 HCDR1

<400> SEQUENCE: 23

Gly Tyr Ser Phe Thr Asp Tyr Asn
1               5

<210> SEQ ID NO 24
<211> LENGTH: 8
<212> TYPE: PRT
<213> ORGANISM: Artificial Sequence
<220> FEATURE:
<223> OTHER INFORMATION: F7 HCDR2

<400> SEQUENCE: 24

Ile Asp Pro Asn Tyr Gly Thr Thr
1               5

<210> SEQ ID NO 25
<211> LENGTH: 11
<212> TYPE: PRT
<213> ORGANISM: Artificial Sequence
<220> FEATURE:
<223> OTHER INFORMATION: F7 HCDR3

<400> SEQUENCE: 25

Ala Ile Lys Gly Tyr Gly Asn Pro Ala Ala Tyr
1               5                   10

<210> SEQ ID NO 26
<211> LENGTH: 8
<212> TYPE: PRT
<213> ORGANISM: Artificial Sequence
<220> FEATURE:
<223> OTHER INFORMATION: F8 HCDR1

<400> SEQUENCE: 26

Gly Phe Thr Leu Ser Thr Tyr Ala

```
<210> SEQ ID NO 27
<211> LENGTH: 8
<212> TYPE: PRT
<213> ORGANISM: Artificial Sequence
<220> FEATURE:
<223> OTHER INFORMATION: F8 HCDR2

<400> SEQUENCE: 27

Ile Ser Gly Gly Gly Gly Asp Thr
1               5

<210> SEQ ID NO 28
<211> LENGTH: 14
<212> TYPE: PRT
<213> ORGANISM: Artificial Sequence
<220> FEATURE:
<223> OTHER INFORMATION: F8 HCDR3

<400> SEQUENCE: 28

Ala Arg Gln Ser His Tyr Gly Ser Ser Tyr Tyr Phe Asp Asn
1               5                   10

<210> SEQ ID NO 29
<211> LENGTH: 8
<212> TYPE: PRT
<213> ORGANISM: Artificial Sequence
<220> FEATURE:
<223> OTHER INFORMATION: F10 HCDR1

<400> SEQUENCE: 29

Gly Tyr Ala Phe Ser Ser Ser Trp
1               5

<210> SEQ ID NO 30
<211> LENGTH: 8
<212> TYPE: PRT
<213> ORGANISM: Artificial Sequence
<220> FEATURE:
<223> OTHER INFORMATION: F10 HCDR2

<400> SEQUENCE: 30

Ile Tyr Pro Gly Asp Gly Tyr Thr
1               5

<210> SEQ ID NO 31
<211> LENGTH: 13
<212> TYPE: PRT
<213> ORGANISM: Artificial Sequence
<220> FEATURE:
<223> OTHER INFORMATION: F10 HCDR3

<400> SEQUENCE: 31

Thr Arg His Gly Asp Phe Pro Tyr Trp Tyr Phe Asp Val
1               5                   10

<210> SEQ ID NO 32
<211> LENGTH: 8
<212> TYPE: PRT
<213> ORGANISM: Artificial Sequence
<220> FEATURE:
<223> OTHER INFORMATION: F17 HCDR1

<400> SEQUENCE: 32

Gly Phe Thr Phe Ser Asp Phe Gly
1               5
```

```
<210> SEQ ID NO 33
<211> LENGTH: 8
<212> TYPE: PRT
<213> ORGANISM: Artificial Sequence
<220> FEATURE:
<223> OTHER INFORMATION: F17 HCDR2

<400> SEQUENCE: 33

Met Ser Tyr Thr Pro Gly Thr Phe
1               5

<210> SEQ ID NO 34
<211> LENGTH: 10
<212> TYPE: PRT
<213> ORGANISM: Artificial Sequence
<220> FEATURE:
<223> OTHER INFORMATION: F17 HCDR3

<400> SEQUENCE: 34

Ala Arg Val His Val Gly Thr Val Asp Tyr
1               5                   10

<210> SEQ ID NO 35
<211> LENGTH: 8
<212> TYPE: PRT
<213> ORGANISM: Artificial Sequence
<220> FEATURE:
<223> OTHER INFORMATION: F19 HCDR1

<400> SEQUENCE: 35

Gly Phe Thr Phe Ser Asp Tyr Trp
1               5

<210> SEQ ID NO 36
<211> LENGTH: 10
<212> TYPE: PRT
<213> ORGANISM: Artificial Sequence
<220> FEATURE:
<223> OTHER INFORMATION: F19 HCDR2

<400> SEQUENCE: 36

Ile Gly Asn Lys Phe His Asn Tyr Glu Thr
1               5                   10

<210> SEQ ID NO 37
<211> LENGTH: 12
<212> TYPE: PRT
<213> ORGANISM: Artificial Sequence
<220> FEATURE:
<223> OTHER INFORMATION: F19 HCDR3

<400> SEQUENCE: 37

Thr Lys Leu Gly Arg Gly Tyr Tyr Val Met Asp Tyr
1               5                   10

<210> SEQ ID NO 38
<211> LENGTH: 8
<212> TYPE: PRT
<213> ORGANISM: Artificial Sequence
<220> FEATURE:
<223> OTHER INFORMATION: F20 HCDR1

<400> SEQUENCE: 38

Gly Tyr Thr Phe Ala Ser Tyr Tyr
1               5
```

```
<210> SEQ ID NO 39
<211> LENGTH: 8
<212> TYPE: PRT
<213> ORGANISM: Artificial Sequence
<220> FEATURE:
<223> OTHER INFORMATION: F20 HCDR2

<400> SEQUENCE: 39

Ile Asn Pro Arg Ser Gly Gly Thr
1               5

<210> SEQ ID NO 40
<211> LENGTH: 14
<212> TYPE: PRT
<213> ORGANISM: Artificial Sequence
<220> FEATURE:
<223> OTHER INFORMATION: F20 HCDR3

<400> SEQUENCE: 40

Ser Arg Ser Gly Arg Leu Arg Gly Phe Tyr Thr Met Asp Tyr
1               5                   10

<210> SEQ ID NO 41
<211> LENGTH: 6
<212> TYPE: PRT
<213> ORGANISM: Artificial Sequence
<220> FEATURE:
<223> OTHER INFORMATION: F4 LCDR1

<400> SEQUENCE: 41

Gln Asn Ile Asn Asn Asn
1               5

<210> SEQ ID NO 42
<211> LENGTH: 3
<212> TYPE: PRT
<213> ORGANISM: Artificial Sequence
<220> FEATURE:
<223> OTHER INFORMATION: F4 LCDR2

<400> SEQUENCE: 42

Phe Ala Ser
1

<210> SEQ ID NO 43
<211> LENGTH: 10
<212> TYPE: PRT
<213> ORGANISM: Artificial Sequence
<220> FEATURE:
<223> OTHER INFORMATION: F4 LCDR3

<400> SEQUENCE: 43

Gln Gln Ile Tyr Ser Trp Pro Gln Leu Thr
1               5                   10

<210> SEQ ID NO 44
<211> LENGTH: 6
<212> TYPE: PRT
<213> ORGANISM: Artificial Sequence
<220> FEATURE:
<223> OTHER INFORMATION: F5 LCDR1

<400> SEQUENCE: 44

Gln Asp Ile Thr Asn Phe
1               5
```

```
<210> SEQ ID NO 45
<211> LENGTH: 3
<212> TYPE: PRT
<213> ORGANISM: Artificial Sequence
<220> FEATURE:
<223> OTHER INFORMATION: F5 LCDR2

<400> SEQUENCE: 45

Tyr Thr Ser
1

<210> SEQ ID NO 46
<211> LENGTH: 8
<212> TYPE: PRT
<213> ORGANISM: Artificial Sequence
<220> FEATURE:
<223> OTHER INFORMATION: F5 LCDR3

<400> SEQUENCE: 46

Leu Gln Tyr Tyr Asn Leu Trp Thr
1               5

<210> SEQ ID NO 47
<211> LENGTH: 6
<212> TYPE: PRT
<213> ORGANISM: Artificial Sequence
<220> FEATURE:
<223> OTHER INFORMATION: F7 LCDR1

<400> SEQUENCE: 47

Gln Asp Ile Asn Lys Tyr
1               5

<210> SEQ ID NO 48
<211> LENGTH: 3
<212> TYPE: PRT
<213> ORGANISM: Artificial Sequence
<220> FEATURE:
<223> OTHER INFORMATION: F7 LCDR2

<400> SEQUENCE: 48

Tyr Thr Ser
1

<210> SEQ ID NO 49
<211> LENGTH: 8
<212> TYPE: PRT
<213> ORGANISM: Artificial Sequence
<220> FEATURE:
<223> OTHER INFORMATION: F7 LCDR3

<400> SEQUENCE: 49

Leu Gln Tyr Tyr Asn Leu Trp Thr
1               5

<210> SEQ ID NO 50
<211> LENGTH: 6
<212> TYPE: PRT
<213> ORGANISM: Artificial Sequence
<220> FEATURE:
<223> OTHER INFORMATION: F8 LCDR1

<400> SEQUENCE: 50

Glu Asn Ile Asp Ser Tyr
1               5

<210> SEQ ID NO 51
```

```
<211> LENGTH: 3
<212> TYPE: PRT
<213> ORGANISM: Artificial Sequence
<220> FEATURE:
<223> OTHER INFORMATION: F8 LCDR2

<400> SEQUENCE: 51

Ala Ala Thr
1

<210> SEQ ID NO 52
<211> LENGTH: 9
<212> TYPE: PRT
<213> ORGANISM: Artificial Sequence
<220> FEATURE:
<223> OTHER INFORMATION: F8 LCDR3

<400> SEQUENCE: 52

Gln His Tyr Tyr Thr Thr Pro Pro Thr
1               5

<210> SEQ ID NO 53
<211> LENGTH: 6
<212> TYPE: PRT
<213> ORGANISM: Artificial Sequence
<220> FEATURE:
<223> OTHER INFORMATION: F10 LCDR1

<400> SEQUENCE: 53

Glu Asn Ile Asp Ser Tyr
1               5

<210> SEQ ID NO 54
<211> LENGTH: 3
<212> TYPE: PRT
<213> ORGANISM: Artificial Sequence
<220> FEATURE:
<223> OTHER INFORMATION: F10 LCDR2

<400> SEQUENCE: 54

Ala Ala Thr
1

<210> SEQ ID NO 55
<211> LENGTH: 9
<212> TYPE: PRT
<213> ORGANISM: Artificial Sequence
<220> FEATURE:
<223> OTHER INFORMATION: F10 LCDR3

<400> SEQUENCE: 55

Gln His His Tyr Ser Thr Pro Pro Thr
1               5

<210> SEQ ID NO 56
<211> LENGTH: 6
<212> TYPE: PRT
<213> ORGANISM: Artificial Sequence
<220> FEATURE:
<223> OTHER INFORMATION: F17 LCDR1

<400> SEQUENCE: 56

Gln Asn Ile Asn Asn Asn
1               5

<210> SEQ ID NO 57
<211> LENGTH: 3
```

```
<212> TYPE: PRT
<213> ORGANISM: Artificial Sequence
<220> FEATURE:
<223> OTHER INFORMATION: F17 LCDR2

<400> SEQUENCE: 57

Tyr Ala Ser
1

<210> SEQ ID NO 58
<211> LENGTH: 10
<212> TYPE: PRT
<213> ORGANISM: Artificial Sequence
<220> FEATURE:
<223> OTHER INFORMATION: F17 LCDR3

<400> SEQUENCE: 58

Gln Gln Ser Asn Ser Trp Pro Ala Leu Thr
1               5                   10

<210> SEQ ID NO 59
<211> LENGTH: 6
<212> TYPE: PRT
<213> ORGANISM: Artificial Sequence
<220> FEATURE:
<223> OTHER INFORMATION: F19 LCDR1

<400> SEQUENCE: 59

Gln Asp Ile Thr Asn His
1               5

<210> SEQ ID NO 60
<211> LENGTH: 3
<212> TYPE: PRT
<213> ORGANISM: Artificial Sequence
<220> FEATURE:
<223> OTHER INFORMATION: F19 LCDR2

<400> SEQUENCE: 60

Tyr Thr Ser
1

<210> SEQ ID NO 61
<211> LENGTH: 9
<212> TYPE: PRT
<213> ORGANISM: Artificial Sequence
<220> FEATURE:
<223> OTHER INFORMATION: F19 LCDR3

<400> SEQUENCE: 61

Gln Gln Asp Ser Gln His Pro Trp Thr
1               5

<210> SEQ ID NO 62
<211> LENGTH: 6
<212> TYPE: PRT
<213> ORGANISM: Artificial Sequence
<220> FEATURE:
<223> OTHER INFORMATION: F20 LCDR1

<400> SEQUENCE: 62

Glu Asn Val Gly Ser Tyr
1               5

<210> SEQ ID NO 63
<211> LENGTH: 3
<212> TYPE: PRT
```

```
<213> ORGANISM: Artificial Sequence
<220> FEATURE:
<223> OTHER INFORMATION: F20 LCDR2

<400> SEQUENCE: 63

Gly Ala Ser
1

<210> SEQ ID NO 64
<211> LENGTH: 8
<212> TYPE: PRT
<213> ORGANISM: Artificial Sequence
<220> FEATURE:
<223> OTHER INFORMATION: F20 LCDR3

<400> SEQUENCE: 64

Gly Gln Thr Tyr Arg Phe Leu Thr
1               5

<210> SEQ ID NO 65
<211> LENGTH: 10
<212> TYPE: PRT
<213> ORGANISM: Artificial Sequence
<220> FEATURE:
<223> OTHER INFORMATION: F4 HCDR1

<400> SEQUENCE: 65

Gly Phe Thr Phe Ser Asp Tyr Gly Met His
1               5                   10

<210> SEQ ID NO 66
<211> LENGTH: 17
<212> TYPE: PRT
<213> ORGANISM: Artificial Sequence
<220> FEATURE:
<223> OTHER INFORMATION: F4 HCDR2

<400> SEQUENCE: 66

Phe Ile Ser Ser Gly Ser Asn Thr Ile Tyr Tyr Ala Asp Ile Val Lys
1               5                   10                  15
Gly

<210> SEQ ID NO 67
<211> LENGTH: 10
<212> TYPE: PRT
<213> ORGANISM: Artificial Sequence
<220> FEATURE:
<223> OTHER INFORMATION: F4 HCDR3

<400> SEQUENCE: 67

Ala Arg Leu Ala Glu Trp Asp Val Ala Tyr
1               5                   10

<210> SEQ ID NO 68
<211> LENGTH: 10
<212> TYPE: PRT
<213> ORGANISM: Artificial Sequence
<220> FEATURE:
<223> OTHER INFORMATION: F5 HCDR1

<400> SEQUENCE: 68

Gly Phe Thr Phe Ser Asn Tyr Gly Met Ser
1               5                   10

<210> SEQ ID NO 69
<211> LENGTH: 17
```

```
<212> TYPE: PRT
<213> ORGANISM: Artificial Sequence
<220> FEATURE:
<223> OTHER INFORMATION: F5 HCDR2

<400> SEQUENCE: 69

Thr Ile Ser Ser Gly Gly Ser Tyr Thr Tyr Tyr Pro Asp Ser Val Lys
1               5                   10                  15

Gly

<210> SEQ ID NO 70
<211> LENGTH: 11
<212> TYPE: PRT
<213> ORGANISM: Artificial Sequence
<220> FEATURE:
<223> OTHER INFORMATION: F5 HCDR3

<400> SEQUENCE: 70

Ser Thr Gln Gly Ser Ser Gly Tyr Val Gly Tyr
1               5                   10

<210> SEQ ID NO 71
<211> LENGTH: 10
<212> TYPE: PRT
<213> ORGANISM: Artificial Sequence
<220> FEATURE:
<223> OTHER INFORMATION: F7 HCDR1

<400> SEQUENCE: 71

Gly Tyr Ser Phe Thr Asp Tyr Asn Met Asn
1               5                   10

<210> SEQ ID NO 72
<211> LENGTH: 17
<212> TYPE: PRT
<213> ORGANISM: Artificial Sequence
<220> FEATURE:
<223> OTHER INFORMATION: F7 HCDR2

<400> SEQUENCE: 72

Val Ile Asp Pro Asn Tyr Gly Thr Thr Asn Tyr Asn Gln Lys Phe Val
1               5                   10                  15

Gly

<210> SEQ ID NO 73
<211> LENGTH: 11
<212> TYPE: PRT
<213> ORGANISM: Artificial Sequence
<220> FEATURE:
<223> OTHER INFORMATION: F7 HCDR3

<400> SEQUENCE: 73

Ala Ile Lys Gly Tyr Gly Asn Pro Ala Ala Tyr
1               5                   10

<210> SEQ ID NO 74
<211> LENGTH: 10
<212> TYPE: PRT
<213> ORGANISM: Artificial Sequence
<220> FEATURE:
<223> OTHER INFORMATION: F8 HCDR1

<400> SEQUENCE: 74

Gly Phe Thr Leu Ser Thr Tyr Ala Met Ser
1               5                   10
```

<210> SEQ ID NO 75
<211> LENGTH: 17
<212> TYPE: PRT
<213> ORGANISM: Artificial Sequence
<220> FEATURE:
<223> OTHER INFORMATION: F8 HCDR2

<400> SEQUENCE: 75

Thr Ile Ser Gly Gly Gly Gly Asp Thr Tyr His Leu Asp Thr Val Lys
1               5                   10                  15
Gly

<210> SEQ ID NO 76
<211> LENGTH: 14
<212> TYPE: PRT
<213> ORGANISM: Artificial Sequence
<220> FEATURE:
<223> OTHER INFORMATION: F8 HCDR3

<400> SEQUENCE: 76

Ala Arg Gln Ser His Tyr Gly Ser Ser Tyr Tyr Phe Asp Asn
1               5                   10

<210> SEQ ID NO 77
<211> LENGTH: 10
<212> TYPE: PRT
<213> ORGANISM: Artificial Sequence
<220> FEATURE:
<223> OTHER INFORMATION: F10 HCDR1

<400> SEQUENCE: 77

Gly Tyr Ala Phe Ser Ser Ser Trp Met Asn
1               5                   10

<210> SEQ ID NO 78
<211> LENGTH: 17
<212> TYPE: PRT
<213> ORGANISM: Artificial Sequence
<220> FEATURE:
<223> OTHER INFORMATION: F10 HCDR2

<400> SEQUENCE: 78

Arg Ile Tyr Pro Gly Asp Gly Tyr Thr His Tyr Asn Gly Met Phe Lys
1               5                   10                  15
Gly

<210> SEQ ID NO 79
<211> LENGTH: 13
<212> TYPE: PRT
<213> ORGANISM: Artificial Sequence
<220> FEATURE:
<223> OTHER INFORMATION: F10 HCDR3

<400> SEQUENCE: 79

Thr Arg His Gly Asp Phe Pro Tyr Trp Tyr Phe Asp Val
1               5                   10

<210> SEQ ID NO 80
<211> LENGTH: 10
<212> TYPE: PRT
<213> ORGANISM: Artificial Sequence
<220> FEATURE:
<223> OTHER INFORMATION: F17 HCDR1

<400> SEQUENCE: 80

```
Gly Phe Thr Phe Ser Asp Phe Gly Met His
1               5                   10

<210> SEQ ID NO 81
<211> LENGTH: 17
<212> TYPE: PRT
<213> ORGANISM: Artificial Sequence
<220> FEATURE:
<223> OTHER INFORMATION: F17 HCDR2

<400> SEQUENCE: 81

Tyr Met Ser Tyr Thr Pro Gly Thr Phe His Tyr Ala Asp Thr Val Lys
1               5                   10                  15

Asp

<210> SEQ ID NO 82
<211> LENGTH: 10
<212> TYPE: PRT
<213> ORGANISM: Artificial Sequence
<220> FEATURE:
<223> OTHER INFORMATION: F17 HCDR3

<400> SEQUENCE: 82

Ala Arg Val His Val Gly Thr Val Asp Tyr
1               5                   10

<210> SEQ ID NO 83
<211> LENGTH: 10
<212> TYPE: PRT
<213> ORGANISM: Artificial Sequence
<220> FEATURE:
<223> OTHER INFORMATION: F19 HCDR1

<400> SEQUENCE: 83

Gly Phe Thr Phe Ser Asp Tyr Trp Met Asn
1               5                   10

<210> SEQ ID NO 84
<211> LENGTH: 19
<212> TYPE: PRT
<213> ORGANISM: Artificial Sequence
<220> FEATURE:
<223> OTHER INFORMATION: F19 HCDR2

<400> SEQUENCE: 84

Gln Ile Gly Asn Lys Phe His Asn Tyr Glu Thr Tyr Tyr Ser Asp Ser
1               5                   10                  15

Val Lys Gly

<210> SEQ ID NO 85
<211> LENGTH: 12
<212> TYPE: PRT
<213> ORGANISM: Artificial Sequence
<220> FEATURE:
<223> OTHER INFORMATION: F19 HCDR3

<400> SEQUENCE: 85

Thr Lys Leu Gly Arg Gly Tyr Tyr Val Met Asp Tyr
1               5                   10

<210> SEQ ID NO 86
<211> LENGTH: 10
<212> TYPE: PRT
<213> ORGANISM: Artificial Sequence
<220> FEATURE:
<223> OTHER INFORMATION: F20 HCDR1
```

<400> SEQUENCE: 86

Gly Tyr Thr Phe Ala Ser Tyr Tyr Leu Tyr
1               5                   10

<210> SEQ ID NO 87
<211> LENGTH: 17
<212> TYPE: PRT
<213> ORGANISM: Artificial Sequence
<220> FEATURE:
<223> OTHER INFORMATION: F20 HCDR2

<400> SEQUENCE: 87

Glu Ile Asn Pro Arg Ser Gly Gly Thr Asn Phe Asn Glu Lys Phe Lys
1               5                   10                  15

Ser

<210> SEQ ID NO 88
<211> LENGTH: 14
<212> TYPE: PRT
<213> ORGANISM: Artificial Sequence
<220> FEATURE:
<223> OTHER INFORMATION: F20 HCDR3

<400> SEQUENCE: 88

Ser Arg Ser Gly Arg Leu Arg Gly Phe Tyr Thr Met Asp Tyr
1               5                   10

<210> SEQ ID NO 89
<211> LENGTH: 11
<212> TYPE: PRT
<213> ORGANISM: Artificial Sequence
<220> FEATURE:
<223> OTHER INFORMATION: F4 LCDR1

<400> SEQUENCE: 89

Arg Ala Ser Gln Asn Ile Asn Asn Asn Leu His
1               5                   10

<210> SEQ ID NO 90
<211> LENGTH: 7
<212> TYPE: PRT
<213> ORGANISM: Artificial Sequence
<220> FEATURE:
<223> OTHER INFORMATION: F4 LCDR2

<400> SEQUENCE: 90

Phe Ala Ser Gln Ser Ile Ser
1               5

<210> SEQ ID NO 91
<211> LENGTH: 10
<212> TYPE: PRT
<213> ORGANISM: Artificial Sequence
<220> FEATURE:
<223> OTHER INFORMATION: F4 LCDR3

<400> SEQUENCE: 91

Gln Gln Ile Tyr Ser Trp Pro Gln Leu Thr
1               5                   10

<210> SEQ ID NO 92
<211> LENGTH: 11
<212> TYPE: PRT
<213> ORGANISM: Artificial Sequence
<220> FEATURE:

<223> OTHER INFORMATION: F5 LCDR1

<400> SEQUENCE: 92

Lys Ala Ser Gln Asp Ile Thr Asn Phe Ile Gly
1               5                   10

<210> SEQ ID NO 93
<211> LENGTH: 7
<212> TYPE: PRT
<213> ORGANISM: Artificial Sequence
<220> FEATURE:
<223> OTHER INFORMATION: F5 LCDR2

<400> SEQUENCE: 93

Tyr Thr Ser Ile Leu Glu Ser
1               5

<210> SEQ ID NO 94
<211> LENGTH: 8
<212> TYPE: PRT
<213> ORGANISM: Artificial Sequence
<220> FEATURE:
<223> OTHER INFORMATION: F5 LCDR3

<400> SEQUENCE: 94

Leu Gln Tyr Tyr Asn Leu Trp Thr
1               5

<210> SEQ ID NO 95
<211> LENGTH: 11
<212> TYPE: PRT
<213> ORGANISM: Artificial Sequence
<220> FEATURE:
<223> OTHER INFORMATION: F7 LCDR1

<400> SEQUENCE: 95

Lys Ala Ser Gln Asp Ile Asn Lys Tyr Leu Ala
1               5                   10

<210> SEQ ID NO 96
<211> LENGTH: 7
<212> TYPE: PRT
<213> ORGANISM: Artificial Sequence
<220> FEATURE:
<223> OTHER INFORMATION: F7 LCDR2

<400> SEQUENCE: 96

Tyr Thr Ser Ile Leu Glu Ser
1               5

<210> SEQ ID NO 97
<211> LENGTH: 8
<212> TYPE: PRT
<213> ORGANISM: Artificial Sequence
<220> FEATURE:
<223> OTHER INFORMATION: F7 LCDR3

<400> SEQUENCE: 97

Leu Gln Tyr Tyr Asn Leu Trp Thr
1               5

<210> SEQ ID NO 98
<211> LENGTH: 11
<212> TYPE: PRT
<213> ORGANISM: Artificial Sequence
<220> FEATURE:
<223> OTHER INFORMATION: F8 LCDR1

<400> SEQUENCE: 98

Arg Val Ser Glu Asn Ile Asp Ser Tyr Leu Ala
1               5                   10

<210> SEQ ID NO 99
<211> LENGTH: 7
<212> TYPE: PRT
<213> ORGANISM: Artificial Sequence
<220> FEATURE:
<223> OTHER INFORMATION: F8 LCDR2

<400> SEQUENCE: 99

Ala Ala Thr Asn Leu Ala Asp
1               5

<210> SEQ ID NO 100
<211> LENGTH: 9
<212> TYPE: PRT
<213> ORGANISM: Artificial Sequence
<220> FEATURE:
<223> OTHER INFORMATION: F8 LCDR3

<400> SEQUENCE: 100

Gln His Tyr Tyr Thr Thr Pro Pro Thr
1               5

<210> SEQ ID NO 101
<211> LENGTH: 11
<212> TYPE: PRT
<213> ORGANISM: Artificial Sequence
<220> FEATURE:
<223> OTHER INFORMATION: F10 LCDR1

<400> SEQUENCE: 101

Arg Ala Ser Glu Asn Ile Asp Ser Tyr Leu Ala
1               5                   10

<210> SEQ ID NO 102
<211> LENGTH: 7
<212> TYPE: PRT
<213> ORGANISM: Artificial Sequence
<220> FEATURE:
<223> OTHER INFORMATION: F10 LCDR2

<400> SEQUENCE: 102

Ala Ala Thr Asn Leu Ala Val
1               5

<210> SEQ ID NO 103
<211> LENGTH: 9
<212> TYPE: PRT
<213> ORGANISM: Artificial Sequence
<220> FEATURE:
<223> OTHER INFORMATION: F10 LCDR3

<400> SEQUENCE: 103

Gln His His Tyr Ser Thr Pro Pro Thr
1               5

<210> SEQ ID NO 104
<211> LENGTH: 11
<212> TYPE: PRT
<213> ORGANISM: Artificial Sequence
<220> FEATURE:
<223> OTHER INFORMATION: F17 LCDR1

```
<400> SEQUENCE: 104

Arg Ala Ser Gln Asn Ile Asn Asn Leu His
1               5                   10

<210> SEQ ID NO 105
<211> LENGTH: 7
<212> TYPE: PRT
<213> ORGANISM: Artificial Sequence
<220> FEATURE:
<223> OTHER INFORMATION: F17 LCDR2

<400> SEQUENCE: 105

Tyr Ala Ser Gln Ser Ile Ser
1               5

<210> SEQ ID NO 106
<211> LENGTH: 10
<212> TYPE: PRT
<213> ORGANISM: Artificial Sequence
<220> FEATURE:
<223> OTHER INFORMATION: F17 LCDR3

<400> SEQUENCE: 106

Gln Gln Ser Asn Ser Trp Pro Ala Leu Thr
1               5                   10

<210> SEQ ID NO 107
<211> LENGTH: 11
<212> TYPE: PRT
<213> ORGANISM: Artificial Sequence
<220> FEATURE:
<223> OTHER INFORMATION: F19 LCDR1

<400> SEQUENCE: 107

Arg Ala Ser Gln Asp Ile Thr Asn His Leu Asn
1               5                   10

<210> SEQ ID NO 108
<211> LENGTH: 7
<212> TYPE: PRT
<213> ORGANISM: Artificial Sequence
<220> FEATURE:
<223> OTHER INFORMATION: F19 LCDR2

<400> SEQUENCE: 108

Tyr Thr Ser Arg Leu His Ser
1               5

<210> SEQ ID NO 109
<211> LENGTH: 9
<212> TYPE: PRT
<213> ORGANISM: Artificial Sequence
<220> FEATURE:
<223> OTHER INFORMATION: F19 LCDR3

<400> SEQUENCE: 109

Gln Gln Asp Ser Gln His Pro Trp Thr
1               5

<210> SEQ ID NO 110
<211> LENGTH: 11
<212> TYPE: PRT
<213> ORGANISM: Artificial Sequence
<220> FEATURE:
<223> OTHER INFORMATION: F20 LCDR1

<400> SEQUENCE: 110
```

Lys Ala Gly Glu Asn Val Gly Ser Tyr Val Ser
1               5                   10

<210> SEQ ID NO 111
<211> LENGTH: 7
<212> TYPE: PRT
<213> ORGANISM: Artificial Sequence
<220> FEATURE:
<223> OTHER INFORMATION: F20 LCDR2

<400> SEQUENCE: 111

Gly Ala Ser Asn Arg Tyr Thr
1               5

<210> SEQ ID NO 112
<211> LENGTH: 8
<212> TYPE: PRT
<213> ORGANISM: Artificial Sequence
<220> FEATURE:
<223> OTHER INFORMATION: F20 LCDR3

<400> SEQUENCE: 112

Gly Gln Thr Tyr Arg Phe Leu Thr
1               5

<210> SEQ ID NO 113
<211> LENGTH: 118
<212> TYPE: PRT
<213> ORGANISM: Artificial Sequence
<220> FEATURE:
<223> OTHER INFORMATION: F5-H1 Heavy Chain Variable Region

<400> SEQUENCE: 113

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Thr Gln Gly Ser Ser Gly Tyr Val Gly Tyr Trp Gly Gln Gly Thr
            100                 105                 110

Leu Val Thr Val Ser Ser
        115

<210> SEQ ID NO 114
<211> LENGTH: 118
<212> TYPE: PRT
<213> ORGANISM: Artificial Sequence
<220> FEATURE:
<223> OTHER INFORMATION: F5-H2 Heavy Chain Variable Region

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

```
Gly Met Ser Trp Val Arg Gln Ala Pro Gly Lys Gly Leu Glu Trp Val
            35                  40                  45

Ala Thr Ile Ser Ser Gly Gly Ser Tyr Thr Tyr Tyr Pro Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ser Thr Gln Gly Ser Ser Gly Tyr Val Gly Tyr Trp Gly Gln Gly Thr
                100                 105                 110

Leu Val Thr Val Ser Ser
            115

<210> SEQ ID NO 115
<211> LENGTH: 118
<212> TYPE: PRT
<213> ORGANISM: Artificial Sequence
<220> FEATURE:
<223> OTHER INFORMATION: F5-H3 Heavy Chain Variable Region

<400> SEQUENCE: 115

Glu Val Gln Leu Val Glu Ser Gly Gly Gly Leu Val Gln Pro Gly Gly
 1               5                   10                  15

Ser Leu Arg Leu Ser Cys Ala Val Ser Gly Phe Thr Phe Ser Asn Tyr
            20                  25                  30

Gly Met Ser Trp Val Arg Gln Ala Pro Gly Lys Gly Leu Glu Trp Val
            35                  40                  45

Ala Thr Ile Ser Ser Gly Gly Ser Tyr Thr Tyr Tyr Pro Asp Ser Val
        50                  55                  60

Lys Gly Arg Phe Thr Ile Ser Arg Asp Asn Ser Lys Asn Thr Leu Tyr
 65                  70                  75                  80

Leu Gln Met Ser Ser Leu Arg Ala Glu Asp Thr Ala Val Tyr Tyr Cys
                85                  90                  95

Ser Thr Gln Gly Ser Ser Gly Tyr Val Gly Tyr Trp Gly Gln Gly Thr
                100                 105                 110

Leu Val Thr Val Ser Ser
            115

<210> SEQ ID NO 116
<211> LENGTH: 118
<212> TYPE: PRT
<213> ORGANISM: Artificial Sequence
<220> FEATURE:
<223> OTHER INFORMATION: F5-H4 Heavy Chain Variable Region

<400> SEQUENCE: 116

Glu Val Gln Leu Val Glu Ser Gly Gly Gly Leu Val Gln Pro Gly Gly
 1               5                   10                  15

Ser Leu Arg Leu Ser Cys Ala Val Ser Gly Phe Thr Phe Ser Asn Tyr
            20                  25                  30

Gly Met Ser Trp Val Arg Gln Ala Pro Gly Lys Gly Leu Glu Trp Val
            35                  40                  45

Ala Thr Ile Ser Ser Gly Gly Ser Tyr Thr Tyr Tyr Pro Asp Ser Val
        50                  55                  60

Lys Gly Arg Phe Thr Ile Ser Arg Asp Asn Asp Lys Asn Thr Leu Tyr
 65                  70                  75                  80

Leu Gln Met Ser Ser Leu Arg Ala Glu Asp Thr Ala Val Tyr Tyr Cys
```

```
                    85                  90                  95
Ser Thr Gln Gly Ser Ser Gly Tyr Val Gly Tyr Trp Gly Gln Gly Thr
                100                 105                 110

Leu Val Thr Val Ser Ser
        115
```

<210> SEQ ID NO 117
<211> LENGTH: 106
<212> TYPE: PRT
<213> ORGANISM: Artificial Sequence
<220> FEATURE:
<223> OTHER INFORMATION: F5-L1 Light Chain Variable Region

<400> SEQUENCE: 117

```
Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Ile Thr Asn Phe
                20                  25                  30

Ile Gly Trp Tyr Gln His Lys Pro Gly Lys Ala Pro Lys Leu Leu Ile
            35                  40                  45

Ser Tyr Thr Ser Ile Leu Glu Ser Gly Val Pro Ser Arg Phe Ser Gly
        50                  55                  60

Ser Gly Ser Gly Arg Asp Tyr Thr Leu Thr Ile Ser Ser Leu Gln Pro
65                  70                  75                  80

Glu Asp Phe Ala Thr Tyr Tyr Cys Leu Gln Tyr Tyr Asn Leu Trp Thr
                85                  90                  95

Phe Gly Gly Gly Thr Lys Val Glu Ile Lys
                100                 105
```

<210> SEQ ID NO 118
<211> LENGTH: 106
<212> TYPE: PRT
<213> ORGANISM: Artificial Sequence
<220> FEATURE:
<223> OTHER INFORMATION: F5-L2 Light Chain Variable Region

<400> SEQUENCE: 118

```
Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Ile Thr Asn Phe
                20                  25                  30

Ile Gly Trp Tyr Gln His Lys Pro Gly Lys Ala Pro Lys Leu Leu Ile
            35                  40                  45

Ser Tyr Thr Ser Ile Leu Glu Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Tyr Asn Leu Trp Thr
                85                  90                  95

Phe Gly Gly Gly Thr Lys Val Glu Ile Lys
                100                 105
```

<210> SEQ ID NO 119
<211> LENGTH: 120
<212> TYPE: PRT
<213> ORGANISM: Artificial Sequence
<220> FEATURE:
<223> OTHER INFORMATION: F10-H1 Heavy Chain Variable Region

<400> SEQUENCE: 119

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Ile
        35                  40                  45

Gly Arg Ile Tyr Pro Gly Asp Gly Tyr Thr His Tyr Asn Gly Met Phe
    50                  55                  60

Lys Gly Arg Ala Ser Leu Thr Ala Asp Lys Ser Thr Ser Thr Gly Tyr
65                  70                  75                  80

Met Glu Leu Ser Ser Leu Arg Ser Glu Asp Thr Ala Val Phe Phe Cys
                85                  90                  95

Thr Arg His Gly Asp Phe Pro Tyr Trp Tyr Phe Asp Val Trp Gly Arg
            100                 105                 110

Gly Thr Leu Val Thr Val Ser Pro
        115                 120
```

<210> SEQ ID NO 120
<211> LENGTH: 120
<212> TYPE: PRT
<213> ORGANISM: Artificial Sequence
<220> FEATURE:
<223> OTHER INFORMATION: F10-H2 Heavy Chain Variable Region

<400> SEQUENCE: 120

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Ile
        35                  40                  45

Gly Arg Ile Tyr Pro Gly Asp Gly Tyr Thr His Tyr Asn Gly Met Phe
    50                  55                  60

Lys Gly Arg Ala Ser Leu Thr Ala Asp Lys Ser Thr Ser Thr Gly Tyr
65                  70                  75                  80

Met Glu Leu Ser Ser Leu Arg Ser Glu Asp Thr Ala Val Phe Phe Cys
                85                  90                  95

Thr Arg His Gly Asp Phe Pro Tyr Trp Tyr Phe Asp Val Trp Gly Arg
            100                 105                 110

Gly Thr Leu Val Thr Val Ser Ser
        115                 120
```

<210> SEQ ID NO 121
<211> LENGTH: 107
<212> TYPE: PRT
<213> ORGANISM: Artificial Sequence
<220> FEATURE:
<223> OTHER INFORMATION: F10-L1 Light Chain Variable Region

<400> SEQUENCE: 121

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Asn Ile Asp Ser Tyr
            20                  25                  30

Leu Ala Trp Tyr Gln Gln Lys Pro Gly Arg Ala Pro Lys Leu Leu Val
        35                  40                  45

Tyr Ala Ala Thr Asn Leu Ala Val Gly Val Pro Ser Arg Phe Ser Gly
```

```
                50                  55                  60
Ser Gly Ser Gly Thr Glu Tyr Thr Leu Thr Ile Ser Ser Leu Gln Ser
 65                  70                  75                  80

Asp Asp Phe Ala Thr Tyr Tyr Cys Gln His His Tyr Ser Thr Pro Pro
                 85                  90                  95

Thr Phe Gly Gln Gly Thr Lys Leu Glu Ile Lys
            100                 105

<210> SEQ ID NO 122
<211> LENGTH: 107
<212> TYPE: PRT
<213> ORGANISM: Artificial Sequence
<220> FEATURE:
<223> OTHER INFORMATION: F10-L2 Light Chain Variable Region

<400> SEQUENCE: 122

Asp Ile Gln Met Thr Gln Ser Pro Ser Thr Leu Ser Ala Ser Val Gly
  1               5                  10                  15

Asp Arg Val Thr Ile Thr Cys Arg Ala Ser Glu Asn Ile Asp Ser Tyr
                 20                  25                  30

Leu Ala Trp Tyr Gln Gln Lys Pro Gly Arg Ala Pro Lys Leu Leu Val
             35                  40                  45

Tyr Ala Ala Thr Asn Leu Ala Val Gly Val Pro Ser Arg Phe Ser Gly
         50                  55                  60

Ser Gly Ser Gly Thr Glu Tyr Thr Leu Thr Ile Ser Ser Leu Gln Pro
 65                  70                  75                  80

Asp Asp Phe Ala Thr Tyr Tyr Cys Gln His His Tyr Ser Thr Pro Pro
                 85                  90                  95

Thr Phe Gly Gln Gly Thr Lys Leu Glu Ile Lys
            100                 105

<210> SEQ ID NO 123
<211> LENGTH: 107
<212> TYPE: PRT
<213> ORGANISM: Artificial Sequence
<220> FEATURE:
<223> OTHER INFORMATION: F10-L3 Light Chain Variable Region

<400> SEQUENCE: 123

Asp Ile Gln Met Thr Gln Ser Pro Ser Thr Leu Ser Ala Ser Val Gly
  1               5                  10                  15

Asp Arg Val Thr Ile Thr Cys Arg Ala Ser Glu Asn Ile Asp Ser Tyr
                 20                  25                  30

Leu Ala Trp Tyr Gln Gln Lys Pro Gly Arg Ala Pro Lys Leu Leu Val
             35                  40                  45

Tyr Ala Ala Thr Asn Leu Ala Val Gly Val Pro Ser Arg Phe Ser Gly
         50                  55                  60

Ser Gly Ser Gly Thr Glu Tyr Thr Leu Thr Ile Ser Ser Leu Gln Ser
 65                  70                  75                  80

Glu Asp Phe Ala Thr Tyr Tyr Cys Gln His His Tyr Ser Thr Pro Pro
                 85                  90                  95

Thr Phe Gly Gln Gly Thr Lys Leu Glu Ile Lys
            100                 105

<210> SEQ ID NO 124
<211> LENGTH: 117
<212> TYPE: PRT
<213> ORGANISM: Artificial Sequence
<220> FEATURE:
```

<223> OTHER INFORMATION: F17-H1 Heavy Chain Variable Region

<400> SEQUENCE: 124

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Phe Ser Asp Phe
                20                  25                  30

Gly Met His Trp Ile Arg Gln Ala Pro Gly Lys Gly Leu Glu Trp Val
            35                  40                  45

Ala Tyr Met Ser Tyr Thr Pro Gly Thr Phe His Tyr Ala Asp Thr Val
        50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val His Val Gly Thr Val Asp Tyr Trp Gly Gln Gly Thr Leu
            100                 105                 110

Val Thr Val Ser Ser
        115

<210> SEQ ID NO 125
<211> LENGTH: 117
<212> TYPE: PRT
<213> ORGANISM: Artificial Sequence
<220> FEATURE:
<223> OTHER INFORMATION: F17-H2 Heavy Chain Variable Region

<400> SEQUENCE: 125

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Phe
                20                  25                  30

Gly Met His Trp Ile Arg Gln Ala Pro Gly Lys Gly Leu Glu Trp Val
            35                  40                  45

Ala Tyr Met Ser Tyr Thr Pro Gly Thr Phe His Tyr Ala Asp Thr Val
        50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val His Val Gly Thr Val Asp Tyr Trp Gly Gln Gly Thr Leu
            100                 105                 110

Val Thr Val Ser Ser
        115

<210> SEQ ID NO 126
<211> LENGTH: 108
<212> TYPE: PRT
<213> ORGANISM: Artificial Sequence
<220> FEATURE:
<223> OTHER INFORMATION: F17-L1 Light Chain Variable Region

<400> SEQUENCE: 126

Glu Val Val Leu Thr Gln Ser Pro Ala Thr Leu Ser Leu Ser Pro Gly
1               5                   10                  15

Glu Arg Ala Thr Leu Ser Cys Arg Ala Ser Gln Asn Ile Asn Asn Asn
                20                  25                  30

Leu His Trp Phe Gln Gln Lys Pro Gly Gln Ala Pro Arg Leu Leu Ile

```
                35                  40                  45
Lys Tyr Ala Ser Gln Ser Ile Ser Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Phe Cys Gln Gln Ser Asn Ser Trp Pro Ala
                85                  90                  95

Leu Thr Phe Gly Gln Gly Thr Lys Val Glu Ile Lys
                100                 105
```

<210> SEQ ID NO 127
<211> LENGTH: 108
<212> TYPE: PRT
<213> ORGANISM: Artificial Sequence
<220> FEATURE:
<223> OTHER INFORMATION: F17-L2 Light Chain Variable Region

<400> SEQUENCE: 127

```
Glu Val Val Leu Thr Gln Ser Pro Ala Thr Leu Ser Leu Ser Pro Gly
 1               5                  10                  15

Glu Arg Ala Thr Leu Ser Cys Arg Ala Ser Gln Asn Ile Asn Asn Asn
                20                  25                  30

Leu His Trp Phe Gln Gln Lys Pro Gly Gln Ala Pro Arg Leu Leu Ile
                35                  40                  45

Lys Tyr Ala Ser Gln Ser Ile Ser Gly Ile Pro Ala Arg Phe Ser Gly
 50                  55                  60

Ser Gly Ser Gly Thr Asp Phe Thr Leu Thr Ile Ser Ser Leu Glu Thr
 65                  70                  75                  80

Glu Asp Phe Ala Val Tyr Phe Cys Gln Gln Ser Asn Ser Trp Pro Ala
                85                  90                  95

Leu Thr Phe Gly Gln Gly Thr Lys Val Glu Ile Lys
                100                 105
```

<210> SEQ ID NO 128
<211> LENGTH: 121
<212> TYPE: PRT
<213> ORGANISM: Artificial Sequence
<220> FEATURE:
<223> OTHER INFORMATION: F20-H1 Heavy Chain Variable Region

<400> SEQUENCE: 128

```
Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Ala Ser Tyr
                20                  25                  30

Tyr Leu Tyr Trp Val Arg Gln Ala Pro Gly Gln Gly Leu Glu Trp Ile
                35                  40                  45

Gly Glu Ile Asn Pro Arg Ser Gly Gly Thr Asn Phe Asn Glu Lys Phe
 50                  55                  60

Lys Ser Arg Ala Thr Val Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ser Arg Ser Gly Arg Leu Arg Gly Phe Tyr Thr Met Asp Tyr Trp Gly
                100                 105                 110

Gln Gly Thr Leu Val Thr Val Ser Ser
                115                 120
```

```
<210> SEQ ID NO 129
<211> LENGTH: 121
<212> TYPE: PRT
<213> ORGANISM: Artificial Sequence
<220> FEATURE:
<223> OTHER INFORMATION: F20-H2 Heavy Chain Variable Region

<400> SEQUENCE: 129

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ala Ser Tyr
            20                  25                  30

Tyr Leu Tyr Trp Val Arg Gln Ala Pro Gly Gln Gly Leu Glu Trp Ile
        35                  40                  45

Gly Glu Ile Asn Pro Arg Ser Gly Gly Thr Asn Phe Asn Glu Lys Phe
    50                  55                  60

Lys Ser Arg Ala Thr Val Thr Val Asp Ala Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Ser Gly Arg Leu Arg Gly Phe Tyr Thr Met Asp Tyr Trp Gly
            100                 105                 110

Gln Gly Thr Leu Val Thr Val Ser Ser
        115                 120

<210> SEQ ID NO 130
<211> LENGTH: 121
<212> TYPE: PRT
<213> ORGANISM: Artificial Sequence
<220> FEATURE:
<223> OTHER INFORMATION: F20-H3 Heavy Chain Variable Region

<400> SEQUENCE: 130

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ala Ser Tyr
            20                  25                  30

Tyr Leu Tyr Trp Val Arg Gln Ala Pro Gly Gln Gly Leu Glu Trp Ile
        35                  40                  45

Gly Glu Ile Asn Pro Arg Ser Gly Gly Thr Asn Phe Asn Glu Lys Phe
    50                  55                  60

Lys Ser Lys Ala Thr Val Thr Val Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ser Arg Ser Gly Arg Leu Arg Gly Phe Tyr Thr Met Asp Tyr Trp Gly
            100                 105                 110

Gln Gly Thr Leu Val Thr Val Ser Ser
        115                 120

<210> SEQ ID NO 131
<211> LENGTH: 106
<212> TYPE: PRT
<213> ORGANISM: Artificial Sequence
<220> FEATURE:
<223> OTHER INFORMATION: F20-L1 Light Chain Variable Region

<400> SEQUENCE: 131

Asp Ile Val Met Thr Gln Ser Pro Asp Ser Leu Ala Val Ser Leu Gly
```

```
                1               5                  10                 15
            Glu Arg Ala Thr Ile Asn Cys Lys Ala Gly Glu Asn Val Gly Ser Tyr
                                20                 25                 30

Val Ser Trp Tyr Gln Gln Lys Pro Gly Gln Pro Pro Lys Leu Leu Ile
                            35                 40                 45

Tyr Gly Ala Ser Asn Arg Tyr Thr Gly Val Pro Asp Arg Phe Ser Gly
                        50                 55                 60

Ser Gly Ser Ala Thr Asp Phe Thr Leu Thr Ile Ser Ser Leu Gln Ala
             65                 70                 75                 80

Glu Asp Val Ala Val Tyr Tyr Cys Gly Gln Thr Tyr Arg Phe Leu Thr
                                85                 90                 95

Phe Gly Gln Gly Thr Lys Val Glu Ile Lys
                            100                105

<210> SEQ ID NO 132
<211> LENGTH: 106
<212> TYPE: PRT
<213> ORGANISM: Artificial Sequence
<220> FEATURE:
<223> OTHER INFORMATION: F20-L2 Light Chain Variable Region

<400> SEQUENCE: 132

Asp Ile Val Met Thr Gln Ser Pro Asp Ser Leu Ala Val Ser Leu Gly
             1               5                  10                 15

Glu Arg Ala Thr Ile Asn Cys Lys Ala Gly Glu Asn Val Gly Ser Tyr
                                20                 25                 30

Val Ser Trp Tyr Gln Gln Lys Pro Gly Gln Ser Pro Lys Leu Leu Ile
                            35                 40                 45

Tyr Gly Ala Ser Asn Arg Tyr Thr Gly Val Pro Asp Arg Phe Ser Gly
                        50                 55                 60

Ser Gly Ser Ala Thr Asp Phe Thr Leu Thr Ile Ser Ser Leu Gln Ala
             65                 70                 75                 80

Glu Asp Val Ala Val Tyr Tyr Cys Gly Gln Thr Tyr Arg Phe Leu Thr
                                85                 90                 95

Phe Gly Gln Gly Thr Lys Val Glu Ile Lys
                            100                105

<210> SEQ ID NO 133
<211> LENGTH: 106
<212> TYPE: PRT
<213> ORGANISM: Artificial Sequence
<220> FEATURE:
<223> OTHER INFORMATION: F20-L3 Light Chain Variable Region

<400> SEQUENCE: 133

Asp Ile Gln Met Thr Gln Ser Pro Ser Thr Leu Ser Ala Ser Val Gly
             1               5                  10                 15

Asp Arg Val Thr Ile Thr Cys Lys Ala Gly Glu Asn Val Gly Ser Tyr
                                20                 25                 30

Val Ser Trp Tyr Gln Gln Lys Pro Gly Lys Ala Pro Lys Leu Leu Ile
                            35                 40                 45

Tyr Gly Ala Ser Asn Arg Tyr Thr Gly Val Pro Ala Arg Phe Ser Gly
                        50                 55                 60

Ser Gly Ser Ala Thr Glu Phe Thr Leu Thr Ile Ser Ser Leu Gln Pro
             65                 70                 75                 80

Asp Asp Phe Ala Thr Tyr Tyr Cys Gly Gln Thr Tyr Arg Phe Leu Thr
                                85                 90                 95
```

```
Phe Gly Gln Gly Thr Lys Val Glu Val Lys
            100                 105

<210> SEQ ID NO 134
<211> LENGTH: 106
<212> TYPE: PRT
<213> ORGANISM: Artificial Sequence
<220> FEATURE:
<223> OTHER INFORMATION: F20-L4 Light Chain Variable Region

<400> SEQUENCE: 134

Asp Ile Gln Met Thr Gln Ser Pro Ser Thr Leu Ser Ala Ser Val Gly
1               5                   10                  15

Asp Arg Val Thr Ile Thr Cys Lys Ala Gly Glu Asn Val Gly Ser Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Ala Arg Phe Ser Gly
    50                  55                  60

Ser Gly Ser Ala Thr Glu Phe Thr Leu Thr Ile Ser Ser Leu Gln Pro
65                  70                  75                  80

Glu Asp Phe Ala Thr Tyr Tyr Cys Gly Gln Thr Tyr Arg Phe Leu Thr
                85                  90                  95

Phe Gly Gln Gly Thr Lys Val Glu Val Lys
            100                 105

<210> SEQ ID NO 135
<211> LENGTH: 257
<212> TYPE: PRT
<213> ORGANISM: Homo sapiens

<400> SEQUENCE: 135

Met Ala Gln Arg Met Thr Thr Gln Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
```

-continued

```
            195                 200                 205
Cys Ile Gln Met Trp Phe Asp Pro Ala Gln Gly Asn Pro Asn Glu Glu
        210                 215                 220

Val Ala Arg Phe Tyr Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser
```

ANTI-FOLATE RECEPTOR 1 ANTIBODIES AND USES THEREOF

CROSS REFERENCE TO RELATED APPLICATIONS

This application is a Section 371 of International Application No. PCT/US2019/021084, filed Mar. 7, 2019, which published in the English language on Sep. 19, 2019 under International Publication No. WO 2019/177854 A1, which claims priority to U.S. Provisional Application No. 62/642,213, filed Mar. 13, 2018. Each disclosure is incorporated herein by reference in its entirety.

FIELD OF THE INVENTION

This invention relates to monoclonal anti-folate receptor 1 (FOLR1) antibodies, nucleic acids and expression vectors encoding the antibodies, recombinant cells containing the vectors, and compositions comprising the antibodies. Methods of making the antibodies, and methods of using the antibodies to treat diseases including cancer are also provided.

This application contains a sequence listing, which is submitted electronically via EFS-Web as an ASCII formatted sequence listing with a file name "065799_11US2_Sequence_Listing" and a creation date of Aug. 18, 2020 and having a size of 61 kb. The sequence listing submitted via EFS-Web is part of the specification and is herein incorporated by reference in its entirety.

BACKGROUND OF THE INVENTION

Folate receptor 1 (FOLR1), also known as folate receptor α (FRα) or folate binding protein (FBP), is a glycosylphosphatidylinositol (GPI)-anchored membrane protein on cell surface that has high affinity for and transports the active form of folate, 5-methyltetrahydrofolate (5-MTF), and its derivatives into cells (Salazar and Ratnam, Cancer Metastasis Rev 2007; 26:141-52). FOLR1 has become an oncology target because it is overexpressed in certain solid tumors such as ovarian, lung and breast cancers (Toffoli et al., Int J Cancer 1997; 74:193-198 and Boogerd et al., Oncotarget 2016; 7:17442-17454), but its expression is at low levels in limited normal human tissues (Weitman, et al., Cancer Res 1992; 52:3396-3401). Consistent with this observation, phase 1 clinical trials conducted so far with FOLR1-targeted small and large molecules revealed good drug tolerability (Cheung et al., Oncotarget 2016; 7:52553-52574). Therefore, FOLR1 is a tumor-associated/tumor-specific antigen and anti-FOLR1 monoclonal antibodies (mAbs) can be used as potential anti-cancer therapeutics.

BRIEF SUMMARY OF THE INVENTION

In one general aspect, the invention relates to isolated monoclonal antibodies or antigen-binding fragments thereof that specifically bind FOLR1.

Provided are isolated monoclonal antibodies or antigen-binding fragments thereof comprising a heavy chain complementarity determining region 1 (HCDR1), HCDR2, HCDR3, a light chain complementarity determining region 1 (LCDR1), LCDR2, and LCDR3, having the polypeptide sequences of:
 a. SEQ ID NOs: 38, 39, 40, 62, 63 and 64, respectively;
 b. SEQ ID NOs: 17, 18, 19, 41, 42 and 43, respectively;
 c. SEQ ID NOs: 20, 21, 22, 44, 45 and 46, respectively;
 d. SEQ ID NOs: 23, 24, 25, 47, 48 and 49, respectively;
 e. SEQ ID NOs: 26, 27, 28, 50, 51 and 52, respectively;
 f. SEQ ID NOs: 29, 30, 31, 53, 54 and 55, respectively;
 g. SEQ ID NOs: 32, 33, 34, 56, 57 and 58, respectively; or
 h. SEQ ID NOs: 35, 36, 37, 59, 60 and 61, respectively;
wherein the antibody or antigen-binding fragment thereof specifically binds FOLR1, preferably human FOLR1.

Provided are isolated monoclonal antibodies or antigen-binding fragments thereof comprising a heavy chain complementarity determining region 1 (HCDR1), HCDR2, HCDR3, a light chain complementarity determining region 1 (LCDR1), LCDR2, and LCDR3, having the polypeptide sequences of:
 a. SEQ ID NOs: 86, 87, 88, 110, 111 and 112, respectively;
 b. SEQ ID NOs: 65, 66, 67, 89, 90 and 91, respectively;
 c. SEQ ID NOs: 68, 69, 70, 92, 93 and 94, respectively;
 d. SEQ ID NOs: 71, 72, 73, 95, 96 and 97, respectively;
 e. SEQ ID NOs: 74, 75, 76, 98, 99 and 100, respectively;
 f. SEQ ID NOs: 77, 78, 79, 101, 102 and 103, respectively;
 g. SEQ ID NOs: 80, 81, 82, 104, 105 and 106, respectively; or
 h. SEQ ID NOs: 83, 84, 85, 107, 108 and 109, respectively;
wherein the antibody or antigen-binding fragment thereof specifically binds FOLR1, preferably human FOLR1.

In certain embodiments, the isolated monoclonal antibody or antigen-binding fragment thereof comprises a heavy chain variable region having a polypeptide sequence at least 95%, at least 96%, at least 97%, at least 98%, or at least 99% identical to SEQ ID NO: 15, 1, 3, 5, 7, 9, 11 or 13, or a light chain variable region having a polypeptide sequence at least 95%, at least 96%, at least 97%, at least 98%, or at least 99% identical to SEQ ID NO: 16, 2, 4, 6, 8, 10, 12 or 14.

In certain embodiments, the isolated monoclonal antibody or antigen-binding fragment thereof comprises:
 a. a heavy chain variable region having the polypeptide sequence of SEQ ID NO:15, and a light chain variable region having the polypeptide sequence of SEQ ID NO:16;
 b. a heavy chain variable region having the polypeptide sequence of SEQ ID NO:1, and a light chain variable region having the polypeptide sequence of SEQ ID NO:2;
 c. a heavy chain variable region having the polypeptide sequence of SEQ ID NO:3, and a light chain variable region having the polypeptide sequence of SEQ ID NO:4;
 d. a heavy chain variable region having the polypeptide sequence of SEQ ID NO:5, and a light chain variable region having the polypeptide sequence of SEQ ID NO:6;
 e. a heavy chain variable region having the polypeptide sequence of SEQ ID NO:7, and a light chain variable region having the polypeptide sequence of SEQ ID NO:8;
 f. a heavy chain variable region having the polypeptide sequence of SEQ ID NO:9, and a light chain variable region having the polypeptide sequence of SEQ ID NO:10;
 g. a heavy chain variable region having the polypeptide sequence of SEQ ID NO:11, and a light chain variable region having the polypeptide sequence of SEQ ID NO:12; or h. a heavy chain variable region having the polypeptide sequence of SEQ ID NO:13, and a light chain variable region having the polypeptide sequence of SEQ ID NO:14.

In certain embodiments, the isolated monoclonal antibody or antigen-binding fragment thereof is chimeric.

In certain embodiments, the isolated monoclonal antibody or antigen-binding fragment thereof is human or humanized. In certain embodiments, the humanized monoclonal antibody or antigen-binding fragment thereof comprises:

(1) a heavy chain variable region having the polypeptide sequence of SEQ ID NO:113, and a light chain variable region having the polypeptide sequence of SEQ ID NO:117;

(2) a heavy chain variable region having the polypeptide sequence of SEQ ID NO:113, and a light chain variable region having the polypeptide sequence of SEQ ID NO:118;

(3) a heavy chain variable region having the polypeptide sequence of SEQ ID NO:114, and a light chain variable region having the polypeptide sequence of SEQ ID NO:117;

(4) a heavy chain variable region having the polypeptide sequence of SEQ ID NO:114, and a light chain variable region having the polypeptide sequence of SEQ ID NO:118;

(5) a heavy chain variable region having the polypeptide sequence of SEQ ID NO:115, and a light chain variable region having the polypeptide sequence of SEQ ID NO:117;

(6) a heavy chain variable region having the polypeptide sequence of SEQ ID NO:115, and a light chain variable region having the polypeptide sequence of SEQ ID NO:118;

(7) a heavy chain variable region having the polypeptide sequence of SEQ ID NO:116, and a light chain variable region having the polypeptide sequence of SEQ ID NO:117;

(8) a heavy chain variable region having the polypeptide sequence of SEQ ID NO:116, and a light chain variable region having the polypeptide sequence of SEQ ID NO:118;

(9) a heavy chain variable region having the polypeptide sequence of SEQ ID NO:119, and a light chain variable region having the polypeptide sequence of SEQ ID NO:121;

(10) a heavy chain variable region having the polypeptide sequence of SEQ ID NO:119, and a light chain variable region having the polypeptide sequence of SEQ ID NO:122;

(11) a heavy chain variable region having the polypeptide sequence of SEQ ID NO:119, and a light chain variable region having the polypeptide sequence of SEQ ID NO:123;

(12) a heavy chain variable region having the polypeptide sequence of SEQ ID NO:120, and a light chain variable region having the polypeptide sequence of SEQ ID NO:121;

(13) a heavy chain variable region having the polypeptide sequence of SEQ ID NO:120, and a light chain variable region having the polypeptide sequence of SEQ ID NO:122;

(14) a heavy chain variable region having the polypeptide sequence of SEQ ID NO:120, and a light chain variable region having the polypeptide sequence of SEQ ID NO:123;

(15) a heavy chain variable region having the polypeptide sequence of SEQ ID NO:124, and a light chain variable region having the polypeptide sequence of SEQ ID NO:126;

(16) a heavy chain variable region having the polypeptide sequence of SEQ ID NO:124, and a light chain variable region having the polypeptide sequence of SEQ ID NO:127;

(17) a heavy chain variable region having the polypeptide sequence of SEQ ID NO:128, and a light chain variable region having the polypeptide sequence of SEQ ID NO:131;

(18) a heavy chain variable region having the polypeptide sequence of SEQ ID NO:128, and a light chain variable region having the polypeptide sequence of SEQ ID NO:132;

(19) a heavy chain variable region having the polypeptide sequence of SEQ ID NO:128, and a light chain variable region having the polypeptide sequence of SEQ ID NO:133;

(20) a heavy chain variable region having the polypeptide sequence of SEQ ID NO:128, and a light chain variable region having the polypeptide sequence of SEQ ID NO:134;

(21) a heavy chain variable region having the polypeptide sequence of SEQ ID NO:129, and a light chain variable region having the polypeptide sequence of SEQ ID NO:131;

(22) a heavy chain variable region having the polypeptide sequence of SEQ ID NO:129, and a light chain variable region having the polypeptide sequence of SEQ ID NO:132;

(23) a heavy chain variable region having the polypeptide sequence of SEQ ID NO:129, and a light chain variable region having the polypeptide sequence of SEQ ID NO:133;

(24) a heavy chain variable region having the polypeptide sequence of SEQ ID NO:129, and a light chain variable region having the polypeptide sequence of SEQ ID NO:134;

(25) a heavy chain variable region having the polypeptide sequence of SEQ ID NO:130, and a light chain variable region having the polypeptide sequence of SEQ ID NO:131;

(26) a heavy chain variable region having the polypeptide sequence of SEQ ID NO:130, and a light chain variable region having the polypeptide sequence of SEQ ID NO:132;

(27) a heavy chain variable region having the polypeptide sequence of SEQ ID NO:130, and a light chain variable region having the polypeptide sequence of SEQ ID NO:133; or

(28) a heavy chain variable region having the polypeptide sequence of SEQ ID NO:130, and a light chain variable region having the polypeptide sequence of SEQ ID NO:134.

In certain embodiments, the isolated monoclonal antibody or antigen-binding fragment thereof binds to FOLR1 and is capable of inducing effector-mediated tumor cell lysis.

Also provided are isolated nucleic acids encoding the monoclonal antibodies or antigen-binding fragments thereof of the invention.

Also provided are vectors comprising the isolated nucleic acids encoding the monoclonal antibodies or antigen-binding fragments thereof of the invention.

Also provided are host cells comprising the vectors comprising the isolated nucleic acids encoding the monoclonal antibodies or antigen-binding fragments thereof of the invention.

In certain embodiments, provided is a pharmaceutical composition comprising the isolated monoclonal antibody or antigen-binding fragment thereof of the invention and a pharmaceutically acceptable carrier.

Also provided are methods of treating cancer in a subject in need thereof, comprising administering to the subject the pharmaceutical compositions of the invention. The cancer can be any liquid or solid cancer, for example, it can be selected from, but not limited to, a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

Also provided are methods of producing the monoclonal antibody or antigen-binding fragment thereof of the invention. The methods comprise culturing a cell comprising a nucleic acid encoding the monoclonal antibody or antigen-binding fragment thereof under conditions to produce the monoclonal antibody or antigen-binding fragment thereof and recovering the monoclonal antibody or antigen-binding fragment thereof from the cell or culture.

Also provided are methods of producing a pharmaceutical composition comprising the monoclonal antibody or antigen-binding fragment of the invention. The methods comprise combining the monoclonal antibody or antigen-binding fragment with a pharmaceutically acceptable carrier to obtain the pharmaceutical composition.

Also provided are methods of determining a level of FOLR1 in a subject. The methods comprise (a) obtaining a sample from the subject; (b) contacting the sample with an isolated monoclonal antibody or antigen-binding fragment thereof of the invention; and (c) determining a level of FOLR1 in the subject. The sample can, for example, be a tissue sample or a blood sample. The tissue sample can, for example, be a cancer tissue sample.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

FIG. 8A, data for the humanized F5 mAbs; FIGS. 8B-8D, data for the humanized F10 mAbs; FIG. 8E, data for a humanized F17 mAb; FIGS. 8F-8J, data for the humanized F20 mAbs.

DETAILED DESCRIPTION OF THE INVENTION

Figure 1A:
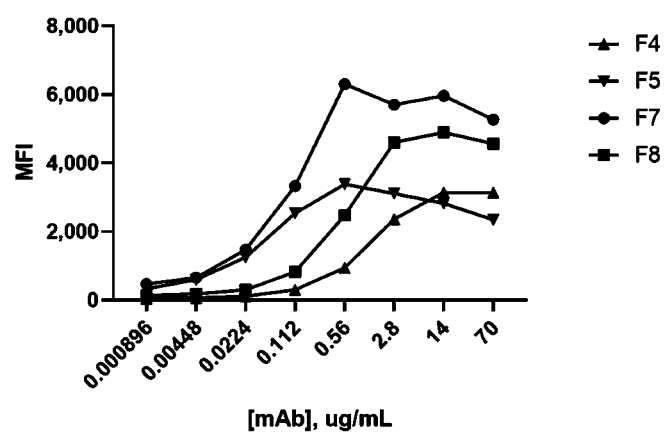
FIGS. 1A-1B show the binding of purified mouse anti-FOLR1 mAbs to CHO cells stably expressing human FOLR1 as demonstrated by FACS analysis.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The words "right," "left," "lower," and "upper" designate directions in the drawings to which reference is made.

It should also be understood that the terms "about," "approximately," "generally," "substantially," and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., anti-FOLR1 antibodies and polynucleotides that encode them, FOLR1 polypeptides and FOLR1 polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

Antibodies

The invention generally relates to isolated anti-FOLR1 antibodies, nucleic acids and expression vectors encoding the antibodies, recombinant cells containing the vectors, and compositions comprising the antibodies. Methods of making the antibodies, and methods of using the antibodies to treat diseases including cancer are also provided. The antibodies of the invention possess one or more desirable functional properties, including but not limited to high-affinity binding to FOLR1, high specificity to FOLR1, and the ability to inhibit tumor growth in subjects in need thereof and in animal models when administered alone or in combination with other anti-cancer therapies.

In a general aspect, the invention relates to isolated monoclonal antibodies or antigen-binding fragments thereof that specifically bind FOLR1.

As used herein, the term "antibody" is used in a broad sense and includes immunoglobulin or antibody molecules including human, humanized, composite and chimeric antibodies and antibody fragments that are monoclonal or polyclonal. In general, antibodies are proteins or peptide chains that exhibit binding specificity to a specific antigen. Antibody structures are well known. Immunoglobulins can be assigned to five major classes (i.e., IgA, IgD, IgE, IgG and IgM), depending on the heavy chain constant domain amino acid sequence. IgA and IgG are further sub-classified as the isotypes IgA1, IgA2, IgG1, IgG2, IgG3 and IgG4. Accordingly, the antibodies of the invention can be of any of the five major classes or corresponding sub-classes. Preferably, the antibodies of the invention are IgG1, IgG2, IgG3 or IgG4. Antibody light chains of vertebrate species can be assigned to one of two clearly distinct types, namely kappa and lambda, based on the amino acid sequences of their constant domains. Accordingly, the antibodies of the invention can contain a kappa or lambda light chain constant domain. According to particular embodiments, the antibodies of the invention include heavy and/or light chain constant regions from rat or human antibodies. In addition to the heavy and light constant domains, antibodies contain an antigen-binding region that is made up of a light chain variable region and a heavy chain variable region, each of which contains three domains (i.e., complementarity determining regions 1-3; CDR1, CDR2, and CDR3). The light chain variable region domains are alternatively referred to as LCDR1, LCDR2, and LCDR3, and the heavy chain variable region domains are alternatively referred to as HCDR1, HCDR2, and HCDR3.

As used herein, the term an "isolated antibody" refers to an antibody which is substantially free of other antibodies having different antigenic specificities (e.g., an isolated antibody that specifically binds to FOLR1 is substantially free of antibodies that do not bind to FOLR1). In addition, an isolated antibody is substantially free of other cellular material and/or chemicals.

As used herein, the term "monoclonal antibody" refers to an antibody obtained from a population of substantially homogeneous antibodies, i.e., the individual antibodies comprising the population are identical except for possible naturally occurring mutations that may be present in minor amounts. The monoclonal antibodies of the invention can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

As used herein, the term "antigen-binding fragment" refers to an antibody fragment such as, for example, a diabody, a Fab, a Fab', a F(ab')2, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multi-specific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment of the heavy chain. According to other particular embodiments, the antigen-binding fragment comprises Fab and F(ab').

As used herein, the term "single-chain antibody" refers to a conventional single-chain antibody in the field, which comprises a heavy chain variable region and a light chain variable region connected by a short peptide of about 15 to about 20 amino acids. As used herein, the term "single domain antibody" refers to a conventional single domain antibody in the field, which comprises a heavy chain variable region and a heavy chain constant region or which comprises only a heavy chain variable region.

As used herein, the term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide.

As used herein, the term "humanized antibody" refers to a non-human antibody that is modified to increase the sequence homology to that of a human antibody, such that the antigen-binding properties of the antibody are retained, but its antigenicity in the human body is reduced.

As used herein, the term "chimeric antibody" refers to an antibody wherein the amino acid sequence of the immunoglobulin molecule is derived from two or more species. The variable region of both the light and heavy chains often corresponds to the variable region of an antibody derived from one species of mammal (e.g., mouse, rat, rabbit, etc.) having the desired specificity, affinity, and capability, while the constant regions correspond to the sequences of an antibody derived from another species of mammal (e.g., human) to avoid eliciting an immune response in that species.

As used herein, the term "multispecific antibody" refers to an antibody that comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes do not overlap or do not substantially overlap. In an embodiment, the first and second epitopes are on different antigens, e.g., the different proteins (or different subunits of a multimeric protein). In an embodiment, a multispecific antibody comprises a third, fourth, or fifth immunoglobulin variable domain. In an embodiment, a multispecific antibody is a bispecific antibody molecule, a trispecific antibody molecule, or a tetraspecific antibody molecule.

As used herein, the term "bispecifc antibody" refers to a multispecific antibody that binds no more than two epitopes or two antigens. A bispecific antibody is characterized by a first immunoglobulin variable domain sequence which has binding specificity for a first epitope and a second immunoglobulin variable domain sequence that has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes are on different antigens, e.g., the different proteins (or different subunits of a multimeric protein). In an embodiment, a bispecific antibody comprises a heavy chain variable domain sequence and a light chain variable domain sequence which have binding specificity for a first epitope and a heavy chain variable domain sequence and a light chain variable domain sequence which have binding specificity for a second epitope. In an embodiment, a bispecific antibody comprises a half antibody, or fragment thereof, having binding specificity for a first epitope and a half antibody, or fragment thereof, having binding specificity for a second epitope. In an embodiment, a bispecific antibody comprises a scFv, or fragment thereof, having binding specificity for a first epitope, and a scFv, or fragment thereof, having binding specificity for a second epitope. In an embodiment, the first epitope is located on FOLR1 and the second epitope is located on PD-1, PD-L1, LAG-3, TIM-3, CTLA-4, EGFR, HER-2, CD19, CD20, CD33, CD47, CD73, apelin, DLL3, claudin18.2, TIP-1, CD3 and/or other tumor associated immune suppressors or surface antigens.

As used herein, the term "FOLR1" refers to folate receptor 1 (FOLR1), also known as folate receptor α (FRα) or folate binding protein (FBP), which is a glycosylphosphatidylinositol (GPI)-anchored membrane protein on a cell surface that has high affinity for and transports the active form of folate, 5-methyltetrahydrofolate (5-MTF), and its derivatives into cells (Salazar and Ratnam, Cancer Metastasis Rev 2007; 26:141-52). FOLR1 has become an oncology target because it is overexpressed in certain solid tumors such as ovarian, lung and breast cancers (Toffoli et al., Int J Cancer 1997; 74:193-198 and Boogerd et al., Oncotarget 2016; 7:17442-17454), but its expression is at low levels in limited normal human tissues (Weitman, et al., Cancer Res 1992; 52:3396-3401). Consistent with this observation, phase 1 clinic trials conducted so far with FOLR1-targeted small and large molecules revealed good drug tolerability (Cheung et al., Oncotarget 2016; 7:52553-52574). Therefore, FOLR1 is a tumor-associated/tumor-specific antigen and anti-FOLR1 monoclonal antibodies (mAbs) can be potential anti-cancer therapies. Further, FOLR1 can be used to specifically target therapeutic molecules to cancer cells. An exemplary amino acid sequence of a human FOLR1 is represented by GenBank Accession No. NP_057937 (SEQ ID NO:135).

As used herein, an antibody that "specifically binds to FOLR1" refers to an antibody that binds to a FOLR1, preferably a human FOLR1, with a KD of $1\times10^{-7}$ M or less, preferably $1\times10^{-8}$ M or less, more preferably $5\times10^{-9}$ M or less, $1\times10^{-9}$ M or less, $5\times10^{-10}$ M or less, or $1\times10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a Biacore® system, or by using bio-layer interferometry technology, such as an Octet RED96 system.

The smaller the value of the KD of an antibody, the higher affinity that the antibody binds to a target antigen.

According to a particular aspect, the invention relates to an isolated monoclonal antibody or antigen-binding fragment thereof comprising a heavy chain complementarity determining region 1 (HCDR1), a HCDR2, a HCDR3, a light chain complementarity determining region 1 (LCDR1), a LCDR2, and a LCDR3, having the polypeptide sequences of:

a. SEQ ID NOs: 38, 39, 40, 62, 63 and 64, respectively;
   b. SEQ ID NOs: 17, 18, 19, 41, 42 and 43, respectively;
   c. SEQ ID NOs: 20, 21, 22, 44, 45 and 46, respectively;
   d. SEQ ID NOs: 23, 24, 25, 47, 48 and 49, respectively;
   e. SEQ ID NOs: 26, 27, 28, 50, 51 and 52, respectively;
   f. SEQ ID NOs: 29, 30, 31, 53, 54 and 55, respectively;
   g. SEQ ID NOs: 32, 33, 34, 56, 57 and 58, respectively; or
   h. SEQ ID NOs: 35, 36, 37, 59, 60 and 61, respectively;

wherein the antibody or antigen-binding fragment thereof specifically binds FOLR1, preferably human FOLR1.

According to a particular aspect, the invention relates to an isolated monoclonal antibody or antigen-binding fragment thereof comprising a heavy chain complementarity determining region 1 (HCDR1), a HCDR2, a HCDR3, a light chain complementarity determining region 1 (LCDR1), a LCDR2, and a LCDR3, having the polypeptide sequences of:

a. SEQ ID NOs: 86, 87, 88, 110, 111 and 112, respectively;
   b. SEQ ID NOs: 65, 66, 67, 89, 90 and 91, respectively;
   c. SEQ ID NOs: 68, 69, 70, 92, 93 and 94, respectively;
   d. SEQ ID NOs: 71, 72, 73, 95, 96 and 97, respectively;
   e. SEQ ID NOs: 74, 75, 76, 98, 99 and 100, respectively;
   f. SEQ ID NOs: 77, 78, 79, 101, 102 and 103, respectively;
   g. SEQ ID NOs: 80, 81, 82, 104, 105 and 106, respectively; or
   h. SEQ ID NOs: 83, 84, 85, 107, 108 and 109, respectively;

wherein the antibody or antigen-binding fragment thereof specifically binds FOLR1, preferably human FOLR1.

According to another particular aspect, the invention relates to an isolated monoclonal antibody or antigen-binding fragment thereof comprising a heavy chain variable region having a polypeptide sequence at least 85%, preferably 90%, more preferably 95% or more, such as 95%, 96%, 97%, 98%, or 99% identical to one of SEQ ID NO: 15, 1, 3, 5, 7, 9, 11 or 13, or a light chain variable region having a polypeptide sequence at least 85%, preferably 90%, more preferably 95% or more, such as 95%, 96%, 97%, 98%, or 99% identical to one of SEQ ID NO: 16, 2, 4, 6, 8, 10, 12 or 14. According to one preferred embodiment, the isolated monoclonal antibody or antigen-binding fragment thereof of the invention comprises a heavy chain variable region having the polypeptide sequence at least 85%, preferably 90%, more preferably 95% or more, such as 95%, 96%, 97%, 98%, or 99% identical to SEQ ID NO: 15, 1, 3, 5, 7, 9, 11 or 13, and a light chain variable region having a polypeptide sequence at least 85%, preferably 90%, more preferably 95% or more, such as 95%, 96%, 97%, 98%, or 99% identical to SEQ ID NO: 16, 2, 4, 6, 8, 10, 12 or 14, respectively.

According to another particular aspect, the invention relates to an isolated monoclonal antibody or antigen-binding fragment thereof of the invention, comprising:
  a. a heavy chain variable region having the polypeptide sequence of SEQ ID NO:15, and a light chain variable region having the polypeptide sequence of SEQ ID NO:16;
  b. a heavy chain variable region having the polypeptide sequence of SEQ ID NO:1, and a light chain variable region having the polypeptide sequence of SEQ ID NO:2;
  c. a heavy chain variable region having the polypeptide sequence of SEQ ID NO:3, and a light chain variable region having the polypeptide sequence of SEQ ID NO:4;
  d. a heavy chain variable region having the polypeptide sequence of SEQ ID NO:5, and a light chain variable region having the polypeptide sequence of SEQ ID NO:6;
  e. a heavy chain variable region having the polypeptide sequence of SEQ ID NO:7, and a light chain variable region having the polypeptide sequence of SEQ ID NO:8;
  f. a heavy chain variable region having the polypeptide sequence of SEQ ID NO:9, and a light chain variable region having the polypeptide sequence of SEQ ID NO:10;
  g. a heavy chain variable region having the polypeptide sequence of SEQ ID NO:11, and a light chain variable region having the polypeptide sequence of SEQ ID NO:12; or
  h. a heavy chain variable region having the polypeptide sequence of SEQ ID NO:13, and a light chain variable region having the polypeptide sequence of SEQ ID NO:14.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 38, 39, 40, 62, 63 and 64, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:15, and a light chain variable region having a polypeptide sequence at least 85%, preferably 90%, more preferably 95% or more, such as 95%, 96%, 97%, 98%, or 99% identical to SEQ ID NO:16. Preferably, the isolated monoclonal antibody or antigen-binding fragment thereof comprises a heavy chain variable region having the polypeptide sequence of SEQ ID NO:15; and a light chain variable region having the polypeptide sequence of SEQ ID NO:16.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 17, 18, 19, 41, 42 and 43, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:1, and a light chain variable region having a polypeptide sequence at least 85%, preferably 90%, more preferably 95% or more, such as 95%, 96%, 97%, 98%, or 99% identical to SEQ ID NO:2. Preferably, the isolated monoclonal antibody or antigen-binding fragment thereof comprises a heavy chain variable region having the polypeptide sequence of SEQ ID NO:1; and a light chain variable region having the polypeptide sequence of SEQ ID NO:2.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 20, 21, 22, 44, 45 and 46, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:3, and a light chain variable region having a polypeptide sequence at least 85%, preferably 90%, more preferably 95% or more, such as 95%, 96%, 97%, 98%, or 99% identical to SEQ ID NO:4. Preferably, the isolated monoclonal antibody or antigen-binding fragment thereof comprises a heavy chain variable region having the polypeptide sequence of SEQ ID NO:3; and a light chain variable region having the polypeptide sequence of SEQ ID NO:4.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 23, 24, 25, 47, 48 and 49, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:5, and a light chain variable region having a polypeptide sequence at least 85%, preferably 90%, more preferably 95% or more, such as 95%, 96%, 97%, 98%, or 99% identical to SEQ ID NO:6. Preferably, the isolated monoclonal antibody or antigen-binding fragment thereof comprises a heavy chain variable region having the polypeptide sequence of SEQ ID NO:5; and a light chain variable region having the polypeptide sequence of SEQ ID NO:6.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 26, 27, 28, 50, 51 and 52, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:7, and a light chain variable region having a polypeptide sequence at least 85%, preferably 90%, more preferably 95% or more, such as 95%, 96%, 97%, 98%, or 99% identical to SEQ ID NO:8. Preferably, the isolated monoclonal antibody or antigen-binding fragment thereof comprises a heavy chain variable region having the polypeptide sequence of SEQ ID NO:7; and a light chain variable region having the polypeptide sequence of SEQ ID NO:8.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 29, 30, 31, 53, 54 and 55, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:9, and a light chain variable region having a polypeptide sequence at least 85%, preferably 90%, more preferably 95% or more, such as 95%, 96%, 97%, 98%, or 99% identical to SEQ ID NO:10. Preferably, the isolated monoclonal antibody or antigen-binding fragment thereof comprises a heavy chain variable region having the polypeptide sequence of SEQ ID NO:9; and a light chain variable region having the polypeptide sequence of SEQ ID NO:10.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 32, 33, 34, 56, 57 and 58, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:11, and a light chain variable region having a polypeptide sequence at least 85%, preferably 90%, more preferably 95% or more, such as 95%, 96%, 97%, 98%, or 99% identical to SEQ ID NO:12. Preferably, the isolated monoclonal antibody or antigen-binding fragment thereof comprises a heavy chain variable region having the polypeptide sequence of SEQ ID NO:11; and a light chain variable region having the polypeptide sequence of SEQ ID NO:12.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 35, 36, 37, 59, 60 and 61, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:13, and a light chain variable region having a polypeptide sequence at least 85%, preferably 90%, more preferably 95% or more, such as 95%, 96%, 97%, 98%, or 99% identical to SEQ ID NO:14. Preferably, the isolated monoclonal antibody or antigen-binding fragment thereof comprises a heavy chain variable region having the polypeptide sequence of SEQ ID NO:13; and a light chain variable region having the polypeptide sequence of SEQ ID NO:14.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 86, 87, 88, 110, 111 and 112, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:15, and a light chain variable region having a polypeptide sequence at least 85%, preferably 90%, more preferably 95% or more, such as 95%, 96%, 97%, 98%, or 99% identical to SEQ ID NO:16. Preferably, the isolated monoclonal antibody or antigen-binding fragment thereof comprises a heavy chain variable region having the polypeptide sequence of SEQ ID NO:15; and a light chain variable region having the polypeptide sequence of SEQ ID NO:16.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 65, 66, 67, 89, 90 and 91, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:1, and a light chain variable region having a polypeptide sequence at least 85%, preferably 90%, more preferably 95% or more, such as 95%, 96%, 97%, 98%, or 99% identical to SEQ ID NO:2. Preferably, the isolated monoclonal antibody or antigen-binding fragment thereof comprises a heavy chain variable region having the polypeptide sequence of SEQ ID NO:1; and a light chain variable region having the polypeptide sequence of SEQ ID NO:2.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 68, 69, 70, 92, 93 and 94, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:3, and a light chain variable region having a polypeptide sequence at least 85%, preferably 90%, more preferably 95% or more, such as 95%, 96%, 97%, 98%, or 99% identical to SEQ ID NO:4. Preferably, the isolated monoclonal antibody or antigen-binding fragment thereof comprises a heavy chain variable region having the polypeptide sequence of SEQ ID NO:3; and a light chain variable region having the polypeptide sequence of SEQ ID NO:4.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 71, 72, 73, 95, 96 and 97, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:5, and a light chain variable region having a polypeptide sequence at least 85%, preferably 90%, more preferably 95% or more, such as 95%, 96%, 97%, 98%, or 99% identical to SEQ ID NO:6. Preferably, the isolated monoclonal antibody or antigen-binding fragment thereof comprises a heavy chain variable region having the polypeptide sequence of SEQ ID NO:5; and a light chain variable region having the polypeptide sequence of SEQ ID NO:6.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 74, 75, 76, 98, 99 and 100, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:7, and a light chain variable region having a polypeptide sequence at least 85%, preferably 90%, more preferably 95% or more, such as 95%, 96%, 97%, 98%, or 99% identical to SEQ ID NO:8. Preferably, the isolated monoclonal antibody or antigen-binding fragment thereof comprises a heavy chain variable region having the polypeptide sequence of SEQ ID NO:7; and a light chain variable region having the polypeptide sequence of SEQ ID NO:8.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 77, 78, 79, 101, 102 and 103, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:9, and a light chain variable region having a polypeptide sequence at least 85%, preferably 90%, more preferably 95% or more, such as 95%, 96%, 97%, 98%, or 99% identical to SEQ ID NO:10. Preferably, the isolated monoclonal antibody or antigen-binding fragment thereof comprises a heavy chain variable region having the polypeptide sequence of SEQ ID NO:9; and a light chain variable region having the polypeptide sequence of SEQ ID NO:10.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 80, 81, 82, 104, 105 and 106, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:11, and a light chain variable region having a polypeptide sequence at least 85%, preferably 90%, more preferably 95% or more, such as 95%, 96%, 97%, 98%, or 99% identical to SEQ ID NO:12. Preferably, the isolated monoclonal antibody or antigen-binding fragment thereof comprises a heavy chain variable region having the polypeptide sequence of SEQ ID NO:11; and a light chain variable region having the polypeptide sequence of SEQ ID NO:12.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 83, 84, 85, 107, 108 and 109, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:13, and a light chain variable region having a polypeptide sequence at least 85%, preferably 90%, more preferably 95% or more, such as 95%, 96%, 97%, 98%, or 99% identical to SEQ ID NO:14. Preferably, the isolated monoclonal antibody or antigen-binding fragment thereof comprises a heavy chain variable region having the polypeptide sequence of SEQ ID NO:13; and a light chain variable region having the polypeptide sequence of SEQ ID NO:14.

According to another particular aspect, the invention relates to an isolated monoclonal antibody or antigen-binding fragment thereof, wherein the antibody or antigen-binding fragment thereof is chimeric.

According to another particular aspect, the invention relates to an isolated monoclonal antibody or antigen-binding fragment thereof, wherein the antibody or antigen-binding fragment thereof is human or humanized.

According to another particular aspect, the humanized monoclonal antibody or antigen-binding fragment thereof comprises:

(1) a heavy chain variable region having the polypeptide sequence of SEQ ID NO:113, and a light chain variable region having the polypeptide sequence of SEQ ID NO:117;

(2) a heavy chain variable region having the polypeptide sequence of SEQ ID NO:113, and a light chain variable region having the polypeptide sequence of SEQ ID NO:118;

(3) a heavy chain variable region having the polypeptide sequence of SEQ ID NO:114, and a light chain variable region having the polypeptide sequence of SEQ ID NO:117;

(4) a heavy chain variable region having the polypeptide sequence of SEQ ID NO:114, and a light chain variable region having the polypeptide sequence of SEQ ID NO:118;

(5) a heavy chain variable region having the polypeptide sequence of SEQ ID NO:115, and a light chain variable region having the polypeptide sequence of SEQ ID NO:117;

(6) a heavy chain variable region having the polypeptide sequence of SEQ ID NO:115, and a light chain variable region having the polypeptide sequence of SEQ ID NO:118;

(7) a heavy chain variable region having the polypeptide sequence of SEQ ID NO:116, and a light chain variable region having the polypeptide sequence of SEQ ID NO:117;

(8) a heavy chain variable region having the polypeptide sequence of SEQ ID NO:116, and a light chain variable region having the polypeptide sequence of SEQ ID NO:118;

(9) a heavy chain variable region having the polypeptide sequence of SEQ ID NO:119, and a light chain variable region having the polypeptide sequence of SEQ ID NO:121;

(10) a heavy chain variable region having the polypeptide sequence of SEQ ID NO:119, and a light chain variable region having the polypeptide sequence of SEQ ID NO:122;

(11) a heavy chain variable region having the polypeptide sequence of SEQ ID NO:119, and a light chain variable region having the polypeptide sequence of SEQ ID NO:123;

(12) a heavy chain variable region having the polypeptide sequence of SEQ ID NO:120, and a light chain variable region having the polypeptide sequence of SEQ ID NO:121;

(13) a heavy chain variable region having the polypeptide sequence of SEQ ID NO:120, and a light chain variable region having the polypeptide sequence of SEQ ID NO:122;
(14) a heavy chain variable region having the polypeptide sequence of SEQ ID NO:120, and a light chain variable region having the polypeptide sequence of SEQ ID NO:123;
(15) a heavy chain variable region having the polypeptide sequence of SEQ ID NO:124, and a light chain variable region having the polypeptide sequence of SEQ ID NO:126;
(16) a heavy chain variable region having the polypeptide sequence of SEQ ID NO:124, and a light chain variable region having the polypeptide sequence of SEQ ID NO:127;
(17) a heavy chain variable region having the polypeptide sequence of SEQ ID NO:128, and a light chain variable region having the polypeptide sequence of SEQ ID NO:131;
(18) a heavy chain variable region having the polypeptide sequence of SEQ ID NO:128, and a light chain variable region having the polypeptide sequence of SEQ ID NO:132;
(19) a heavy chain variable region having the polypeptide sequence of SEQ ID NO:128, and a light chain variable region having the polypeptide sequence of SEQ ID NO:133;
(20) a heavy chain variable region having the polypeptide sequence of SEQ ID NO:128, and a light chain variable region having the polypeptide sequence of SEQ ID NO:134;
(21) a heavy chain variable region having the polypeptide sequence of SEQ ID NO:129, and a light chain variable region having the polypeptide sequence of SEQ ID NO:131;
(22) a heavy chain variable region having the polypeptide sequence of SEQ ID NO:129, and a light chain variable region having the polypeptide sequence of SEQ ID NO:132;
(23) a heavy chain variable region having the polypeptide sequence of SEQ ID NO:129, and a light chain variable region having the polypeptide sequence of SEQ ID NO:133;
(24) a heavy chain variable region having the polypeptide sequence of SEQ ID NO:129, and a light chain variable region having the polypeptide sequence of SEQ ID NO:134;
(25) a heavy chain variable region having the polypeptide sequence of SEQ ID NO:130, and a light chain variable region having the polypeptide sequence of SEQ ID NO:131;
(26) a heavy chain variable region having the polypeptide sequence of SEQ ID NO:130, and a light chain variable region having the polypeptide sequence of SEQ ID NO:132;
(27) a heavy chain variable region having the polypeptide sequence of SEQ ID NO:130, and a light chain variable region having the polypeptide sequence of SEQ ID NO:133; or
(28) a heavy chain variable region having the polypeptide sequence of SEQ ID NO:130, and a light chain variable region having the polypeptide sequence of SEQ ID NO:134.

In another general aspect, the invention relates to an isolated nucleic acid encoding a monoclonal antibody or antigen-binding fragment thereof of the invention. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding monoclonal antibodies or antigen-binding fragments thereof of the invention can be altered without changing the amino acid sequences of the proteins.

In another general aspect, the invention relates to a vector comprising an isolated nucleic acid encoding a monoclonal antibody or antigen-binding fragment thereof of the invention. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to embodiments of the invention. Such techniques are well known to those skilled in the art in view of the present disclosure.

In another general aspect, the invention relates to a host cell comprising an isolated nucleic acid encoding a monoclonal antibody or antigen-binding fragment thereof of the invention. Any host cell known to those skilled in the art in view of the present disclosure can be used for recombinant expression of antibodies or antigen-binding fragments thereof of the invention. In some embodiments, the host cells are *E. coli* TG1 or BL21 cells (for expression of, e.g., an scFv or Fab antibody), CHO-DG44 or CHO-K1 cells or HEK293 cells (for expression of, e.g., a full-length IgG antibody). According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, the invention relates to a method of producing a monoclonal antibody or antigen-binding fragment thereof of the invention, comprising culturing a cell comprising a nucleic acid encoding the monoclonal antibody or antigen-binding fragment thereof under conditions to produce a monoclonal antibody or antigen-binding fragment thereof of the invention, and recovering the antibody or antigen-binding fragment thereof from the cell or cell culture (e.g., from the supernatant). Expressed antibodies or antigen-binding fragments thereof can be harvested from the cells and purified according to conventional techniques known in the art and as described herein.

Pharmaceutical Compositions

In another general aspect, the invention relates to a pharmaceutical composition, comprising an isolated monoclonal antibody or antigen-binding fragment thereof of the invention and a pharmaceutically acceptable carrier. The term "pharmaceutical composition" as used herein means a product comprising an antibody of the invention together with a pharmaceutically acceptable carrier. Antibodies of the invention and compositions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an antibody pharmaceutical composition can be used in the invention.

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carrier can be used in formulating the pharmaceutical compositions of the invention.

In one embodiment of the invention, the pharmaceutical composition is a liquid formulation. A preferred example of a liquid formulation is an aqueous formulation, i.e., a formulation comprising water. The liquid formulation can comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition can be formulated as an injectable which can be injected, for example, via an injection device (e.g., a syringe or an infusion pump). The injection can be delivered subcutaneously, intramuscularly, intraperitoneally, intravitreally, or intravenously, for example.

In another embodiment, the pharmaceutical composition is a solid formulation, e.g., a freeze-dried or spray-dried composition, which can be used as is, or whereto the physician or the patient adds solvents, and/or diluents prior to use. Solid dosage forms can include tablets, such as compressed tablets, and/or coated tablets, and capsules (e.g., hard or soft gelatin capsules). The pharmaceutical composition can also be in the form of sachets, dragees, powders, granules, lozenges, or powders for reconstitution, for example.

The dosage forms may be immediate release, in which case they can comprise a water-soluble or dispersible carrier, or they can be delayed release, sustained release, or modified release, in which case they can comprise water-insoluble polymers that regulate the rate of dissolution of the dosage form in the gastrointestinal tract or under the skin.

In other embodiments, the pharmaceutical composition can be delivered intranasally, intrabuccally, or sublingually.

The pH in an aqueous formulation can be between pH 3 and pH 10. In one embodiment of the invention, the pH of the formulation is from about 7.0 to about 9.5. In another embodiment of the invention, the pH of the formulation is from about 3.0 to about 7.0.

In another embodiment of the invention, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer can be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments of the invention.

In another embodiment of the invention, the pharmaceutical composition comprises a preservative. Non-limiting examples of preservatives include: benzethonium chloride, benzoic acid, benzyl alcohol, bronopol, butyl 4-hydroxybenzoate, chlorobutanol, chlorocresol, chlorohexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomerosal, and mixtures thereof. The preservative can be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments of the invention.

In another embodiment of the invention, the pharmaceutical composition comprises an isotonic agent. Non-limiting examples of the embodiment include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars may be mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethylcellulose. Another example of an isotonic agent is a sugar alcohol, wherein the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. The isotonic agent can be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative embodiments of the invention.

In another embodiment of the invention, the pharmaceutical composition comprises a chelating agent. Non-limiting examples of chelating agents include citric acid, aspartic acid, salts of ethylenediaminetetraacetic acid (EDTA), and mixtures thereof. The chelating agent can be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments of the invention.

In another embodiment of the invention, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment of the invention, the pharmaceutical composition comprises a stabilizer, wherein said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer can be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments of the invention.

In further embodiments of the invention, the pharmaceutical composition comprises one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant can, for example, be selected from the group consisting of anionic surfactants, cationic surfactants, nonionic surfactants, and/or zwitterionic surfactants. The surfactant can be present individually or in the aggregate, in a concentration from about 0.1 mg/ml to about 20 mg/ml. Pharmaceutical compositions comprising each one of these specific surfactants constitute alternative embodiments of the invention.

In a further embodiment of the invention, the pharmaceutical composition comprises one or more protease inhibitors, such as, e.g., EDTA, and/or benzamidine hydrochloric acid (HCl). The protease inhibitor can be present individually or in the aggregate, in a concentration from about 0.1 mg/ml to about 20 mg/ml. Pharmaceutical compositions comprising each one of these specific protease inhibitors constitute alternative embodiments of the invention.

In another general aspect, the invention relates to a method of producing a pharmaceutical composition comprising a monoclonal antibody or antigen-binding fragment thereof of the invention, comprising combining a monoclonal antibody or antigen-binding fragment thereof with a pharmaceutically acceptable carrier to obtain the pharmaceutical composition.

Methods of Use

In another general aspect, the invention relates to a method of targeting FOLR1 on a cancer cell surface in a subject, the method comprising administering to the subject an isolated monoclonal antibody or antigen binding fragment thereof that specifically binds FOLR1 or a pharmaceutical composition of the invention. Binding of the monoclonal antibody or antigen-binding fragment thereof to FOLR1 can mediate complement-dependent cytotoxicity (CDC), antibody-dependent phagocytosis (ADPC), and/or antibody-dependent cellular cytotoxicity (ADCC) or other effects that result in the death of the targeted cancer cell. The monoclonal antibody or antigen-binding fragment thereof can, for example, serve to recruit conjugated drugs, and/or can form a bispecific antibody with another monoclonal antibody to mediate the death of the targeted cancer cell.

The functional activity of antibodies and antigen-binding fragments thereof that bind FOLR1 can be characterized by methods known in the art and as described herein. Methods for characterizing antibodies and antigen-binding fragments thereof that bind FOLR1 include, but are not limited to, affinity and specificity assays including Biacore, ELISA, and OctetRed analysis; binding assays to detect the binding of antibodies to FOLR1 on cancer cells or cells recombinantly expressing FOLR1 by FACS. According to particular embodiments, the methods for characterizing antibodies and antigen-binding fragments thereof that bind FOLR1 include those described below.

In another general aspect, the invention relates to a method of treating a cancer in a subject in need thereof, comprising administering to the subject an isolated monoclonal antibody or antigen binding fragment thereof that specifically binds FOLR1 or a pharmaceutical composition of the invention. The cancer can, for example, be selected from but not limited to, a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

According to embodiments of the invention, the pharmaceutical composition comprises a therapeutically effective amount of an anti-FOLR1 antibody or antigen-binding fragment thereof. As used herein, the term "therapeutically effective amount" refers to an amount of an active ingredient or component that elicits the desired biological or medicinal response in a subject. A therapeutically effective amount can be determined empirically and in a routine manner, in relation to the stated purpose.

As used herein with reference to anti-FOLR1 antibodies or antigen-binding fragments thereof, a therapeutically effective amount means an amount of the anti-FOLR1 antibody or antigen-binding fragment thereof that modulates an immune response in a subject in need thereof.

According to particular embodiments, a therapeutically effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

According to particular embodiments, the compositions described herein are formulated to be suitable for the intended route of administration to a subject. For example, the compositions described herein can be formulated to be suitable for intravenous, subcutaneous, or intramuscular administration.

As used herein, the terms "treat," "treating," and "treatment" are all intended to refer to an amelioration or reversal of at least one measurable physical parameter related to a cancer, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition, such as a tumor or more preferably a cancer. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

According to particular embodiments, provided are compositions used in the treatment of a cancer. For cancer therapy, the compositions can be used in combination with another treatment including, but not limited to, a chemotherapy, an anti-CD20 mAb, an anti-CD47 mAb, an anti-TIM-3 mAb, an anti-LAG-3 mAb, an anti-CD73 mAb, an anti-apelin mAb, an anti-CTLA-4 mAb, an anti-PD-L1 mAb, an anti-PD-1 mAb, a PD-1/PD-L1 therapy, other immuno-oncology drugs, an antiangiogenic agent, a radiation therapy, an antibody-drug conjugate (ADC), a targeted therapy, or other anticancer drugs. Anti-FOLR1 antibodies can be used to construct bispecific antibodies with partner mAbs against PD-1, PD-L1, LAG3, TIM-3, CTLA-4, EGFR, HER-2, CD19, CD20, CD33, CD73, CD47, CD3, apelin, DLL-3, TIP-1, CLDN18.2, and/or other tumor surface antigens to treat cancers/tumors that express both FOLR1 and the specific tumor associated antigen.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

In another general aspect, the invention relates to a method of determining a level of FOLR1 in a subject. The methods comprise (a) obtaining a sample from the subject; (b) contacting the sample with a monoclonal antibody or antigen-binding fragment thereof of the invention; and (c) determining a level of FOLR1 in the subject.

As used herein, "sample" refers to a biological sample isolated from a subject and can include, but is not limited to, whole blood, serum, plasma, blood cells, endothelial cells, tissue biopsies (e.g., a cancer tissue), lymphatic fluid, ascites fluid, interstitial fluid, bone marrow, cerebrospinal fluid, saliva, mucous, sputum, sweat, urine, or any other secretion, excretion, or other bodily fluids. A "blood sample" refers to whole blood or any fraction thereof, including blood cells, serum, and plasma.

In certain embodiments, the level of FOLR1 in the subject can be determined utilizing assays selected from, but not limited to, a Western blot assay, an ELISA assay, and/or an immunohistochemistry (IHC). Relative protein levels can be determined by utilizing Western blot analysis and immunohistochemistry (IHC), and absolute protein levels can be determined by utilizing an ELISA assay. When determining the relative levels of FOLR1, the levels of FOLR1 can be determined between at least two samples, e.g., between samples from the same subject at different time points, between samples from different tissues in the same subject, and/or between samples from different subjects. Alternatively, when determining absolute levels of FOLR1, such as by an ELISA assay, the absolute level of FOLR1 in the sample can be determined by creating a standard for the ELISA assay prior to testing the sample. A person skilled in the art would understand which analytical techniques to utilize to determine the level of FOLR1 in a sample from the subject utilizing the antibodies or antigen-binding fragments thereof of the invention.

Utilizing methods of determining a level of FOLR1 in a sample from a subject can lead to the diagnosis of abnormal (elevated, reduced, or insufficient) FOLR1 levels in a disease and making appropriate therapeutic decisions. Such a disease can include, for example, cancer. Additionally, by monitoring the levels of FOLR1 in a subject, the risk of developing a disease as indicated above can be determined based on the knowledge of the level of FOLR1 in a particular disease and/or during the progression of the particular disease.

EMBODIMENTS

This invention provides the following non-limiting embodiments.

Embodiment 1 is an isolated monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequence of:
  a. SEQ ID NOs: 38, 39, 40, 62, 63 and 64, respectively;
  b. SEQ ID NOs: 17, 18, 19, 41, 42 and 43, respectively;
  c. SEQ ID NOs: 20, 21, 22, 44, 45 and 46, respectively;
  d. SEQ ID NOs: 23, 24, 25, 47, 48 and 49, respectively;
  e. SEQ ID NOs: 26, 27, 28, 50, 51 and 52, respectively;
  f. SEQ ID NOs: 29, 30, 31, 53, 54 and 55, respectively;
  g. SEQ ID NOs: 32, 33, 34, 56, 57 and 58, respectively; or
  h. SEQ ID NOs: 35, 36, 37, 59, 60 and 61, respectively;
wherein the antibody or antigen-binding fragment thereof specifically binds FOLR1, preferably human FOLR1.

Embodiment 2 is an isolated monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequence of:
  a. SEQ ID NOs: 86, 87, 88, 110, 111 and 112, respectively;
  b. SEQ ID NOs: 65, 66, 67, 89, 90 and 91, respectively;
  c. SEQ ID NOs: 68, 69, 70, 92, 93 and 94, respectively;

d. SEQ ID NOs: 71, 72, 73, 95, 96 and 97, respectively;
e. SEQ ID NOs: 74, 75, 76, 98, 99 and 100, respectively;
f. SEQ ID NOs: 77, 78, 79, 101, 102 and 103, respectively;
g. SEQ ID NOs: 80, 81, 82, 104, 105 and 106, respectively; or
h. SEQ ID NOs: 83, 84, 85, 107, 108 and 109, respectively;

wherein the antibody or antigen-binding fragment thereof specifically binds FOLR1, preferably human FOLR1.

Embodiment 3 is the isolated monoclonal antibody or antigen-binding fragment thereof of embodiment 1 or 2, comprising a heavy chain variable region having a polypeptide sequence at least 95%, at least 96%, at least 97%, at least 98%, or at least 99% identical to SEQ ID NO: 15, 1, 3, 5, 7, 9, 11 or 13, or a light chain variable region having a polypeptide sequence at least 95%, at least 96%, at least 97%, at least 98%, or at least 99% identical to SEQ ID NO: 16, 2, 4, 6, 8, 10, 12 or 14.

Embodiment 4 is the isolated monoclonal antibody or antigen-binding fragment thereof of embodiments 1-3, comprising:
  a. a heavy chain variable region having the polypeptide sequence of SEQ ID NO:15, and a light chain variable region having the polypeptide sequence of SEQ ID NO:16;
  b. a heavy chain variable region having the polypeptide sequence of SEQ ID NO:1, and a light chain variable region having the polypeptide sequence of SEQ ID NO:2;
  c. a heavy chain variable region having the polypeptide sequence of SEQ ID NO:3, and a light chain variable region having the polypeptide sequence of SEQ ID NO:4;
  d. a heavy chain variable region having the polypeptide sequence of SEQ ID NO:5, and a light chain variable region having the polypeptide sequence of SEQ ID NO:6;
  e. a heavy chain variable region having the polypeptide sequence of SEQ ID NO:7, and a light chain variable region having the polypeptide sequence of SEQ ID NO:8;
  f. a heavy chain variable region having the polypeptide sequence of SEQ ID NO:9, and a light chain variable region having the polypeptide sequence of SEQ ID NO:10;
  g. a heavy chain variable region having the polypeptide sequence of SEQ ID NO:11, and a light chain variable region having the polypeptide sequence of SEQ ID NO:12; or
  h. a heavy chain variable region having the polypeptide sequence of SEQ ID NO:13, and a light chain variable region having the polypeptide sequence of SEQ ID NO:14.

Embodiment 5 is the isolated monoclonal antibody or antigen-binding fragment thereof of any one of embodiments 1-4, wherein the antibody or antigen-binding fragment thereof is chimeric.

Embodiment 6 is the isolated monoclonal antibody or antigen-binding fragment thereof of any one of embodiments 1-5, wherein the antibody or antigen-binding fragment thereof is human or humanized.

Embodiment 7 is the isolated monoclonal antibody or antigen-binding fragment thereof of any one of embodiments 6, wherein the humanized monoclonal antibody or antigen-binding fragment thereof comprises:

(1) a heavy chain variable region having the polypeptide sequence of SEQ ID NO:113, and a light chain variable region having the polypeptide sequence of SEQ ID NO:117;
(2) a heavy chain variable region having the polypeptide sequence of SEQ ID NO:113, and a light chain variable region having the polypeptide sequence of SEQ ID NO:118;
(3) a heavy chain variable region having the polypeptide sequence of SEQ ID NO:114, and a light chain variable region having the polypeptide sequence of SEQ ID NO:117;
(4) a heavy chain variable region having the polypeptide sequence of SEQ ID NO:114, and a light chain variable region having the polypeptide sequence of SEQ ID NO:118;
(5) a heavy chain variable region having the polypeptide sequence of SEQ ID NO:115, and a light chain variable region having the polypeptide sequence of SEQ ID NO:117;
(6) a heavy chain variable region having the polypeptide sequence of SEQ ID NO:115, and a light chain variable region having the polypeptide sequence of SEQ ID NO:118;
(7) a heavy chain variable region having the polypeptide sequence of SEQ ID NO:116, and a light chain variable region having the polypeptide sequence of SEQ ID NO:117;
(8) a heavy chain variable region having the polypeptide sequence of SEQ ID NO:116, and a light chain variable region having the polypeptide sequence of SEQ ID NO:118;
(9) a heavy chain variable region having the polypeptide sequence of SEQ ID NO:119, and a light chain variable region having the polypeptide sequence of SEQ ID NO:121;
(10) a heavy chain variable region having the polypeptide sequence of SEQ ID NO:119, and a light chain variable region having the polypeptide sequence of SEQ ID NO:122;
(11) a heavy chain variable region having the polypeptide sequence of SEQ ID NO:119, and a light chain variable region having the polypeptide sequence of SEQ ID NO:123;
(12) a heavy chain variable region having the polypeptide sequence of SEQ ID NO:120, and a light chain variable region having the polypeptide sequence of SEQ ID NO:121;
(13) a heavy chain variable region having the polypeptide sequence of SEQ ID NO:120, and a light chain variable region having the polypeptide sequence of SEQ ID NO:122;
(14) a heavy chain variable region having the polypeptide sequence of SEQ ID NO:120, and a light chain variable region having the polypeptide sequence of SEQ ID NO:123;
(15) a heavy chain variable region having the polypeptide sequence of SEQ ID NO:124, and a light chain variable region having the polypeptide sequence of SEQ ID NO:126;
(16) a heavy chain variable region having the polypeptide sequence of SEQ ID NO:124, and a light chain variable region having the polypeptide sequence of SEQ ID NO:127;
(17) a heavy chain variable region having the polypeptide sequence of SEQ ID NO:128, and a light chain variable region having the polypeptide sequence of SEQ ID NO:131;

(18) a heavy chain variable region having the polypeptide sequence of SEQ ID NO:128, and a light chain variable region having the polypeptide sequence of SEQ ID NO:132;
(19) a heavy chain variable region having the polypeptide sequence of SEQ ID NO:128, and a light chain variable region having the polypeptide sequence of SEQ ID NO:133;
(20) a heavy chain variable region having the polypeptide sequence of SEQ ID NO:128, and a light chain variable region having the polypeptide sequence of SEQ ID NO:134;
(21) a heavy chain variable region having the polypeptide sequence of SEQ ID NO:129, and a light chain variable region having the polypeptide sequence of SEQ ID NO:131;
(22) a heavy chain variable region having the polypeptide sequence of SEQ ID NO:129, and a light chain variable region having the polypeptide sequence of SEQ ID NO:132;
(23) a heavy chain variable region having the polypeptide sequence of SEQ ID NO:129, and a light chain variable region having the polypeptide sequence of SEQ ID NO:133;
(24) a heavy chain variable region having the polypeptide sequence of SEQ ID NO:129, and a light chain variable region having the polypeptide sequence of SEQ ID NO:134;
(25) a heavy chain variable region having the polypeptide sequence of SEQ ID NO:130, and a light chain variable region having the polypeptide sequence of SEQ ID NO:131;
(26) a heavy chain variable region having the polypeptide sequence of SEQ ID NO:130, and a light chain variable region having the polypeptide sequence of SEQ ID NO:132;
(27) a heavy chain variable region having the polypeptide sequence of SEQ ID NO:130, and a light chain variable region having the polypeptide sequence of SEQ ID NO:133; or
(28) a heavy chain variable region having the polypeptide sequence of SEQ ID NO:130, and a light chain variable region having the polypeptide sequence of SEQ ID NO:134.

Embodiment 8 is an isolated monoclonal antibody or antigen-binding fragment thereof of any one of embodiments 1-7, wherein the monoclonal antibody or antigen-binding fragment thereof is capable of binding FOLR1 and inducing effector-mediated tumor cell lysis.

Embodiment 9 is an isolated nucleic acid encoding the monoclonal antibody or antigen-binding fragment thereof of any one of embodiments 1-8.

Embodiment 10 is a vector comprising the isolated nucleic acid of embodiment 9.

Embodiment 11 is a host cell comprising the vector of embodiment 10.

Embodiment 12 is a pharmaceutical composition, comprising the isolated monoclonal antibody or antigen-binding fragment thereof of any one of embodiments 1-8 and a pharmaceutically acceptable carrier.

Embodiment 13 is a method of treating cancer in a subject in need thereof, comprising administering to the subject the pharmaceutical composition of embodiment 12.

Embodiment 14 is a method of targeting FOLR1 on a cancer cell surface in a subject in need thereof, the method comprising administering to the subject the pharmaceutical composition of embodiment 12.

Embodiment 15 is a method of producing the monoclonal antibody or antigen-binding fragment thereof of any one of embodiments 1-8, comprising culturing a cell comprising a nucleic acid encoding the monoclonal antibody or antigen-binding fragment thereof under conditions to produce the monoclonal antibody or antigen-binding fragment thereof and recovering the monoclonal antibody or antigen-binding fragment thereof from the cell or culture.

Embodiment 16 is a method of producing a pharmaceutical composition comprising the monoclonal antibody or antigen-binding fragment of any one of embodiments 1-8, comprising combining the monoclonal antibody or antigen-binding fragment thereof with a pharmaceutically acceptable carrier to obtain the pharmaceutical composition.

Embodiment 17 is a method of determining a level of FOLR1 in a subject, the method comprising:
 a. obtaining a sample from the subject;
 b. contacting the sample with an isolated monoclonal antibody or antigen-binding fragment thereof of any one of embodiments 1-8; and
 c. determining a level of FOLR1 in the subject.

Embodiment 18 is the method of embodiment 17, wherein the sample is a tissue sample.

Embodiment 19 is the method of embodiment 18, wherein the tissue sample is a cancer tissue sample.

Embodiment 20 is the method of embodiment 17, wherein the sample is a blood sample.

EXAMPLES

Example 1: Identification of Anti-FOLR1 Monoclonal Antibodies

Mice were immunized with a fusion protein containing human FOLR1 (Arg25 to Met233) fused at the C-terminus with human Fc (huFOLR1-huFc). Plasma titer was determined by ELISA. After euthanization, lymph nodes and spleen were collected to produce hybridomas. Hybridomas were grown in 96-well tissue culture plates and supernatants from individual wells were screened by ELISA and FACS using CHO cells stably expressing the full-length human FOLR1. Top positive clones were isolated and sequenced.

Sequences of heavy and light chain variable regions for anti-FOLR1 monoclonal antibodies are provided in Tables 1 and 2, and the CDR regions for the anti-FOLR1 monoclonal antibodies are provided in Tables 3-6.

TABLE 1

Sequences of heavy chain variable regions for anti-FOLR1 mAbs

| mAb clones | VH | ID |
|---|---|---|
| F4 | EVQLVESGGGLVKPGGSLKLSCAASGFTFSDYGMHWVRQAPEKGLEWVAFIS SGSNTIYYADIVKGRFAISRDNAKNTLFLQMASLRSEDTALYYCARLAEWDV AYWGQGTLVTVSA | 1 |

TABLE 1-continued

Sequences of heavy chain variable regions for anti-FOLR1 mAbs

| mAb clones | VH | ID |
|---|---|---|
| F5 | EVQLVESGGELVKPGGSLKLSCAVSGFTFSNYGMSWVRQTPDKRLEWVATIS SGGSYTYYPDSVKGRFTISRDNDKNTLYLQMSSLKSEDTAMYYCSTQGSSGY VGYWGQGTTLTVSS | 3 |
| F7 | EFQLQQSGPELVKPGASVKISCKASGYSFTDYNMNWVKQSNGKSLEWIGVIDP NYGTTNYNQKFVGKATLTVDQSSITAYMQLNSLTAEDSAVYFCAIKGYGNPA AYWGQGTLVTVSA | 5 |
| F8 | EVMLVESGGGLVKPGGSLKLSCVASGFTLSTYAMSWVRQTPEKRLEWVATIS GGGGDTYHLDTVKGRFTISRDNAKNTLYLQMSSLRSEDTALYYCARQSHYGS SYYFDNWGQGTTLTVSS | 7 |
| F10 | QVQLQQSGPELVKPGASVKISCKASGYAFSSSWMNWVRQRPGKGLEWIGRIY PGDGYTHYNGMFKGKATLTADKSSSTGYMQLSSLTSEDSAVYFCTRHGDFPY WYFDVWGTGTTVTVSS | 9 |
| F17 | DVQLVESGGGLVQPGGSRKLSCAASGFTFSDFGMHWIRQAPERGLEWVAYM SYTPGTFHYADTVKDRFFISRDNAKNTLFLQMTSLRSDDTAMYYCARVHVGT VDYWGQGTSVTVSS | 11 |
| F19 | EVKLDETGGGLVQPGRPMKLSCVASGFTFSDYWMNWVRQSPDKGLEWVAQI GNKFHNYETYYSDSVKGRFTISRDDSKSSVYLQMNSLRVEDTGIYYCTKLGRG YYVMDYWGQGTSVTVSS | 13 |
| F20 | QVQLQQSGAELVKPGASVQLSCKASGYTFASYYLYWVKQRPGQGLEWIGEIN PRSGGTNFNEKFKSKATVTVDKSSSTAYMQLSSLTSEDSAVYYCSRSGRLRGF YTMDYWGQGTSVTVSS | 15 |

VH: heavy chain variable region;
ID: SEQ ID NO

TABLE 2

Sequences of light chain variable regions for anti-FOLR1 mAbs

| mAb clones | VL | ID |
|---|---|---|
| F4 | DIVLTQSPATLSVTPGDRISLSCRASQNINNNLHWYQQKSHESPRLLIKFASQSI SGIPSRFSGSGSGTDFTLNINGVETEDFGMYFCQQIYSWPQLTFGAGTRLELK | 2 |
| F5 | DIQMTQSPSSLSAFLGGKVTITCKASQDITNFIGWYQHKPGKGPRLLISYTSILE SGIPSRFSGSGSGRDYSFSISNLEPEDIATYYCLQYYNLWTFGGGTKLEIK | 4 |
| F7 | DIQMTQSPSSLSASLGGKVTITCKASQDINKYLAWYQHEPGKGPRLLIRYTSIL ESGIPSRFSGSGSGRDYSFSISNLEPEDIATYYCLQYYNLWTFGGGTKLEIK | 6 |
| F8 | DIQMTQSPASLSASVGEIVTIICRVSENIDSYLAWYQQKQGKSPQLLVYAATNL ADGVPSRFSGSGSGSQYSLKINSLQSEDVARYYCQHYYTTPPTFGGGTKLDIK | 8 |
| F10 | DIQMTQSPASLSASVGESVTITCRASENIDSYLAWYQQKQGKSPQLLVYAATN LAVGVPSRFSGSGSGTQYTLKINSLQSEDVARYYCQHHYSTPPTFGGGTKLEIK | 10 |
| F17 | DVVLTQSPATLSVTPGDSVSLSCRASQNINNNLHWFQQKSHESPRLLIKYASQS ISGIPSRFSGSGSGTDFTLSINNVETEDFGIYFCQQSNSWPALTFGTGTKVELK | 12 |
| F19 | DIQMTQTTSSLSASLGDRVTLNCRASQDITNHLNWFQQKPDGTFQLLIYYTSR LHSGVPSRFSGSGSGTDYSLTISNLEQEDFATYFCQQDSQHPWTFGGGTKLEIK | 14 |

TABLE 2-continued

Sequences of light chain variable regions for anti-FOLR1 mAbs

| mAb clones | VL | ID |
|---|---|---|
| F20 | NIVMTQSPKSMSVSVGERVTLSCKAGENVGSYVSWYQQKPEQSPELLIYGAS NRYTGVPDRFTGSGSATDFTLTISSVQAEDLADYYCGQTYRFLTFGAGTKLEL K | 16 |

VL: light chain variable region;
ID: SEQ ID NO

TABLE 3

CDR regions 1-3 of heavy chain for anti-FOLR1 mAbs

| mAb clones | HC CDR1 | ID | HC CDR2 | ID | HC CDR3 | ID |
|---|---|---|---|---|---|---|
| F4 | GFTFSDYG | 17 | ISSGSNTI | 18 | ARLAEWDVAY | 19 |
| F5 | GFTFSNYG | 20 | ISSGGSYT | 21 | STQGSSGYVGY | 22 |
| F7 | GYSFTDYN | 23 | IDPNYGTT | 24 | AIKGYGNPAAY | 25 |
| F8 | GFTLSTYA | 26 | ISGGGGDT | 27 | ARQSHYGSSYYFDN | 28 |
| F10 | GYAFSSSW | 29 | IYPGDGYT | 30 | TRHGDFPYWYFDV | 31 |
| F17 | GFTFSDFG | 32 | MSYTPGTF | 33 | ARVHVGTVDY | 34 |
| F19 | GFTFSDYW | 35 | IGNKFHNYET | 36 | TKLGRGYYVMDY | 37 |
| F20 | GYTFASYY | 38 | INPRSGGT | 39 | SRSGRLRGFYTMDY | 40 |

HC: heavy chain;
CDR: complementarity determining region;
ID: SEQ ID NO
The HC CDRs for the anti-FOLR1 mAbs were determined utilizing the IMGT method (Lefranc, M.-P. et al., Nucleic Acids Res. 1999; 27:209-212).

TABLE 4

CDR regions 1-3 of light chain for anti-FOLR1 mAbs

| mAb clones | LC CDR1 | ID | LC CDR2 | ID | LC CDR3 | ID |
|---|---|---|---|---|---|---|
| F4 | QNINNN | 41 | FAS | 42 | QQIYSWPQLT | 43 |
| F5 | QDITNF | 44 | YTS | 45 | LQYYNLWT | 46 |
| F7 | QDINKY | 47 | YTS | 48 | LQYYNLWT | 49 |
| F8 | ENIDSY | 50 | AAT | 51 | QHYYTTPPT | 52 |
| F10 | ENIDSY | 53 | AAT | 54 | QHHYSTPPT | 55 |
| F17 | QNINNN | 56 | YAS | 57 | QQSNSWPALT | 58 |
| F19 | QDITNH | 59 | YTS | 60 | QQDSQHPWT | 61 |
| F20 | ENVGSY | 62 | GAS | 63 | GQTYRFLT | 64 |

LC: light chain;
CDR: complementanty determining region;
ID: SEQ ID NO
The LC CDRs for the anti-FOLR1 mAbs were determined utilizing the IMGT method (Lefranc, M.-P. et al., Nucleic Acids Res. 1999; 27:209-212).

TABLE 5

CDR regions 1-3 of heavy chain for anti-FOLR1 mAbs

| mAb clone | HC CDR1 | ID | HC CDR2 | ID | HC CDR3 | ID |
|---|---|---|---|---|---|---|
| F4 | GFTFSDYGMH | 65 | FISSGSNTIYYADIVKG | 66 | ARLAEWDVAY | 67 |
| F5 | GFTFSNYGMS | 68 | TISSGGSYTYYPDSVKG | 69 | STQGSSGYVGY | 70 |
| F7 | GYSFTDYNMN | 71 | VIDPNYGTTNYNQKFVG | 72 | AIKGYGNPAAY | 73 |
| F8 | GFTLSTYAMS | 74 | TISGGGGDTYHLDTVKG | 75 | ARQSHYGSSYYFDN | 76 |
| F10 | GYAFSSSWMN | 77 | RIYPGDGYTHYNGMFKG | 78 | TRHGDFPYWYFDV | 79 |
| F17 | GFTFSDFGMH | 80 | YMSYTPGTFHYADTVKD | 81 | ARVHVGTVDY | 82 |
| F19 | GFTFSDYWMN | 83 | QIGNKFHNYETYYSDSVKG | 84 | TKLGRGYYVMDY | 85 |
| F20 | GYTFASYYLY | 86 | EINPRSGGTNFNEKFKS | 87 | SRSGRLRGFYTMDY | 88 |

HC: heavy chain;
CDR complementarity determining region;
ID: SEQ ID NO
The HC CDRs for the anti-FOLR1 mAbs were determined utilizing the Kabat method (Elvin A. Kabat et al., Sequences of Proteins of Immunological Interest 5th ed. (1991))

TABLE 6

CDR regions 1-3 of light chain for anti-FOLR1 mAbs

| mAb clones | LC CDR1 | ID | LC CDR2 | ID | LC CDR3 | ID |
|---|---|---|---|---|---|---|
| F4 | RASQNINNNLH | 89 | FASQSIS | 90 | QQIYSWPQLT | 91 |
| F5 | KASQDITNFIG | 92 | YTSILES | 93 | LQYYNLWT | 94 |
| F7 | KASQDINKYLA | 95 | YTSILES | 96 | LQYYNLWT | 97 |
| F8 | RVSENIDSYLA | 98 | AATNLAD | 99 | QHYYTTPPT | 100 |
| F10 | RASENIDSYLA | 101 | AATNLAV | 102 | QHHYSTPPT | 103 |
| F17 | RASQNINNNLH | 104 | YASQSIS | 105 | QQSNSWPALT | 106 |
| F19 | RASQDFINHLN | 107 | YTSRLHS | 108 | QQDSQHPWT | 109 |
| F20 | KAGENVGSYVS | 110 | GASNRYT | 111 | GQTYRFLT | 112 |

LC: light chain;
CDR: complementarity determining region;
ID: SEQ ID NO
The LC CDRs for the anti-FOLR1 mAbs were determined utilizing the Kabat method (Elvin A. Kabat et al., Sequences of Proteins of Immunological Interest 5th ed. (1991))

Example 2: Production and Purification of mAbs from Hybridoma Supernatants

Mouse anti-FOLR1 mAbs were purified from hybridoma media/supernatants of the positive clones using Protein A affinity chromatography.

Example 3: FACS Binding Analysis of Purified Anti-FOLR1 Mouse Antibodies

Figure 1B:
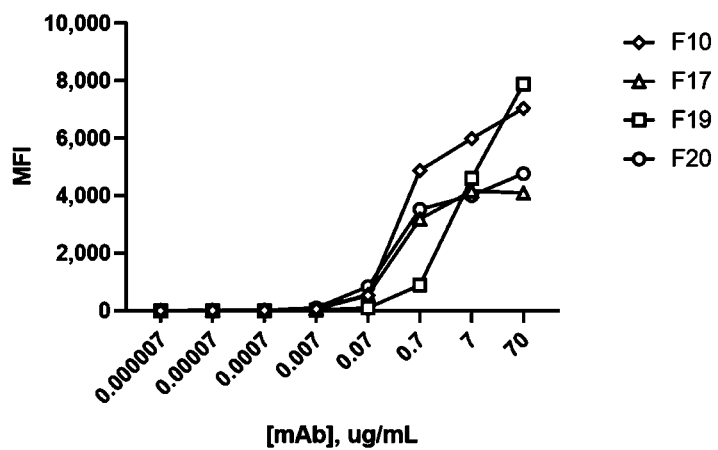

CHO cells stably transfected with full-length human FOLR1 were transferred to a 96-well plate at 200,000 cells/well, washed once with FACS buffer (1×PBS, pH6.8+ 2% FBS) and incubated with purified mouse anti-FOLR1 mAbs from hybridoma supernatants at various concentrations for 15 minutes on ice. Cells were then centrifuged at 1,000 rpm for 5 minutes and washed with FACS buffer three times. The cells were incubated with PE-conjugated goat anti-mouse IgG polyclonal antibodies and incubated on ice for another 15 minutes. Cells were then washed with FACS buffer three times and then resuspended in FACS buffer containing 0.1 µg/ml PI (propidium iodide) for live/dead cell gating. Cells were then run through the FACS Caliber instrument and the data were analyzed by the Flowjo software. Results of the binding of purified mouse anti-FOLR1 mAbs to CHO cells stably expressing human FOLR1 are shown in FIGS. 1A-1B. MFI, mean fluorescence intensity.

Example 4: Production and Purification of Chimeric Anti-FOLR1 mAbs from Culture Media of Transfected 293E Cells To obtain recombinant chimeric anti-FOLR1 mAbs, the expression vectors containing the mouse variable regions (VH and VL) fused to the constant regions of human IgG1 heavy chain and kappa light chain, respectively, were transiently transfected into 293E cells. The recombinant antibodies produced in the suspension of the transfected cells were purified using Protein A affinity chromatography.

Example 5: ELISA Binding Analysis of Purified Chimeric Anti-FOLR1 mAbs

Figure 2A:
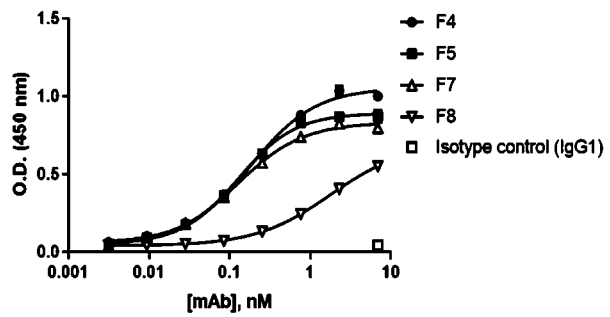
FIGS. 2A-2C show the results for the dose-dependent binding of the chimeric anti-FOLR1 mAbs to immobilized FOLR1 extracellular domain in an ELISA assay.
Figure 2B:
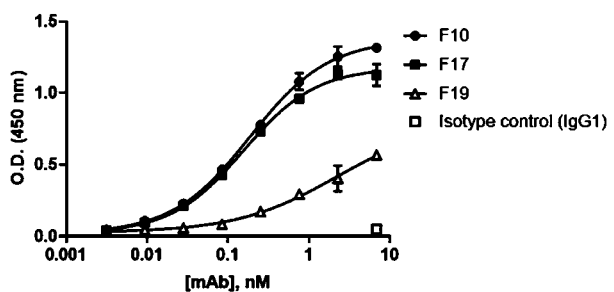
Figure 2C:
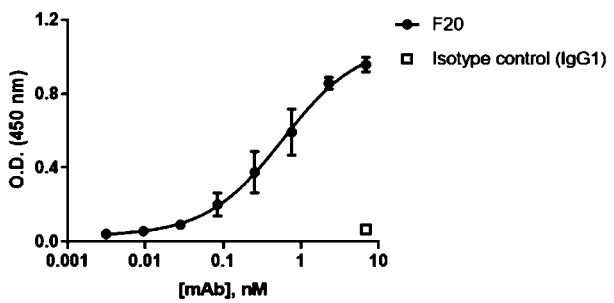
Figure 3A:
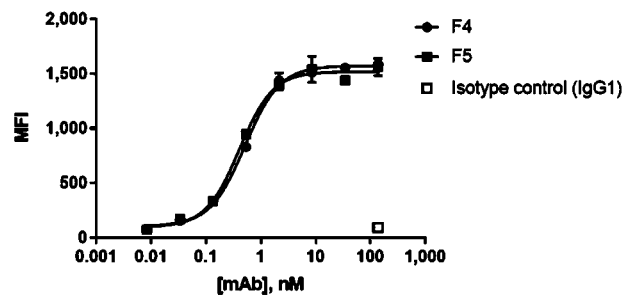
FIGS. 3A-3D show the results for the dose-dependent binding of the chimeric anti-FOLR1 mAbs to SK-OV-3 cells in a FACS assay.
Figure 3B:
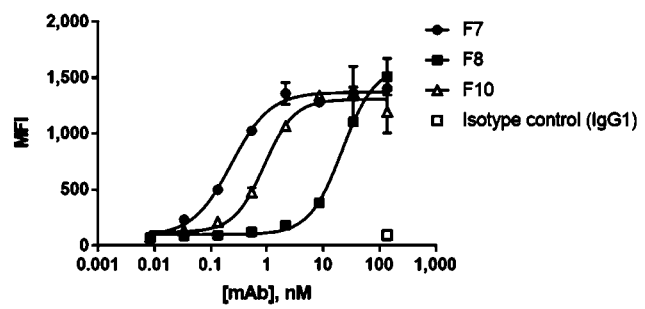
Figure 3C:
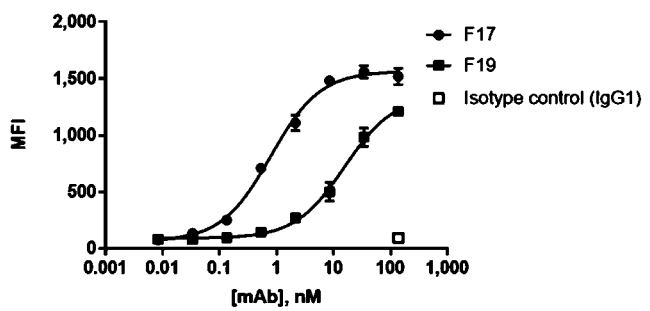
Figure 3D:
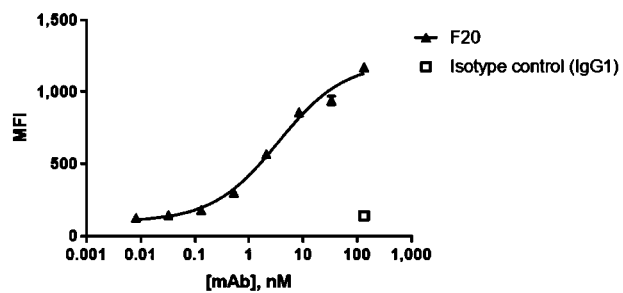

The Purified chimeric mAbs were tested in an ELISA assay for their ability to bind to immobilized human FOLR1. Recombinant extracellular domain of human FOLR1 (Novoprotein, Cat #: C784) in carbonate coating buffer was coated on a 96-well plate at room temperature for 1 hour. The plate is blocked by 5% BSA in TBST for 1 hour at room temperature. In each well of an individual plate, mAbs at various concentrations were incubated for 1 hour at room temperature. The plate was washed and the binding to FOLR1 was detected by anti-human IgG conjugated to horseradish peroxidase (hIgG-HRP) (ThermoFisher Scientific, Cat #: H10007) with incubation for 1 hour at room temperature. Then after washing, the ELISA was developed using One-step Detection Solution (ThermoFisher Scientific, Cat #: 34028) and measured as the absorbance at 450 nm. The results are shown in FIGS. 2A-2C.

Example 6: FACS Binding Analysis of Purified Chimeric Anti-FOLR1 mAbs

To assess the binding of the chimeric anti-FOLR1 mAbs to cells that are known to express FOLR1, SK-OV-3 (ATCC® HTB-77™) cells were plated at 80,000 cells per well on a 96-well non-binding U-bottom plate (Greiner Bio-One, Cat #: 650901). In some experiments, 90,000 cells per well were used. The cells were incubated in 50 µL FACS buffer (HBSS with 0.1% BSA and 0.05% sodium azide) containing mAbs at different concentrations on ice for 15 minutes. After wash, cells were incubated in 50 µL FACS buffer containing 3.5 µg/mL F(ab')2-Goat anti-Human IgG Fc conjugated to Alexa Fluor® 488 (Invitrogen, Cat #: H10120) on ice for 15 minutes in dark and washed again. Cells were analyzed using an Attune NxT flow cytometer. The results for the binding of the chimeric anti-FOLR1 mAbs to SK-OV-3 cells are shown in FIGS. 3A-3D. MFI, mean fluorescence intensity.

Example 7: Biacore Assay with Chimeric Anti-FOLR1 mAbs

The interaction of the chimeric anti-FOLR1 mAbs and FOLR1 was measured by Surface Plasmon Resonance (SPR) (Biacore 8k, GE Healthcare). Briefly, an anti-FOLR1 mAb was immobilized to a protein A sensor chip (GE Healthcare, Cat #: 29-1275-56) in HBS-P buffer (0.01 M HEPES pH 7.4, 0.15 M NaCl, 0.05% v/v Surfactant P20) with an injection flow rate at 10 µL/ml. The recombinant FOLR1 (Novoprotein, Cat #: C784) at variant concentrations was loaded with the flow rate of 30 µL/min in HBS-P buffer. Following antigen loading, the surface was regenerated with 10 mM glycine-HCl (pH 1.5). Sensor grams were fit with a 1:1 binding model using Biacore 8k evaluation software (GE Healthcare). The results of the binding affinity for the anti-FOLR1 mAbs are shown in Table 7.

TABLE 7

KD values for the anti-FOLR1 mAbs from a Biacore assay

| Chimeric mAb | KD (nM) |
|---|---|
| F4 | 0.547 |
| F5 | 0.352 |
| F7 | 2.33 |
| F8 | 0.721 |
| F10 | 0.704 |
| F17 | 0.265 |
| F19 | 11.8 |
| F20 | 1.00 |

Example 8: Humanization of Anti-FOLR1 mAbs

Figure 4A:
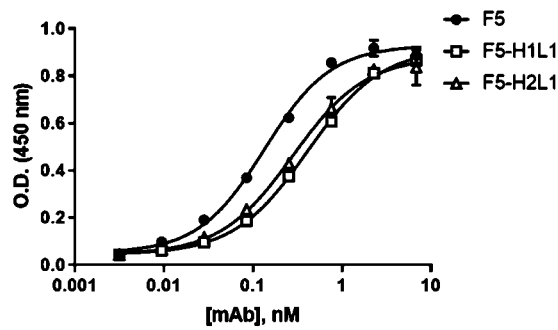
FIGS. 4A-4C show the results for the dose-dependent binding of the humanized F5 mAbs to immobilized FOLR1 extracellular domain in an ELISA assay.
Figure 4B:
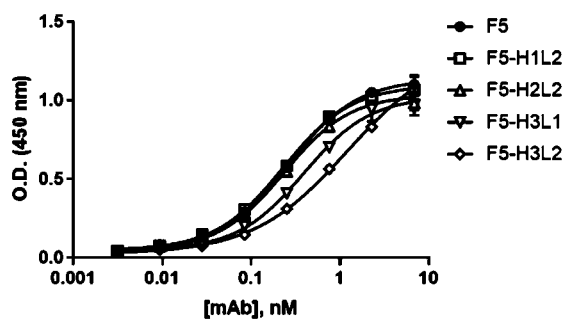
Figure 4C:
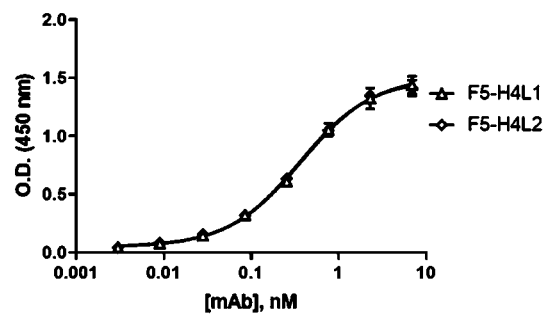
Figure 5A:
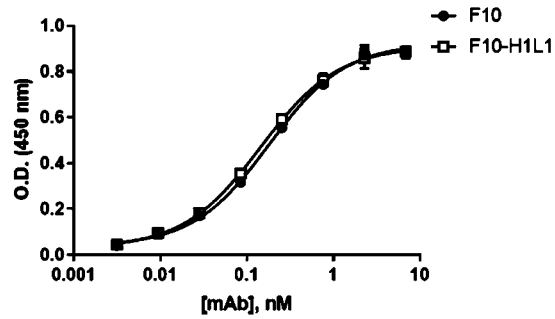
FIGS. 5A-5B show the results for the dose-dependent binding of the humanized F10 mAbs to immobilized FOLR1 extracellular domain in an ELISA assay.
Figure 5B:
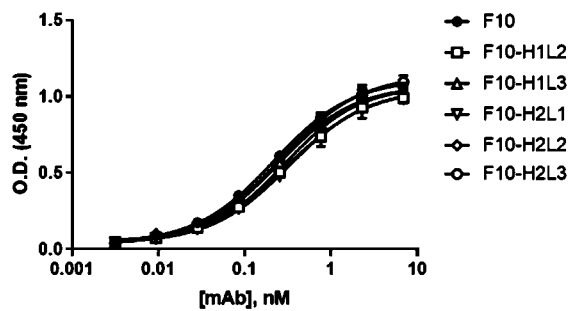
Figure 6A:
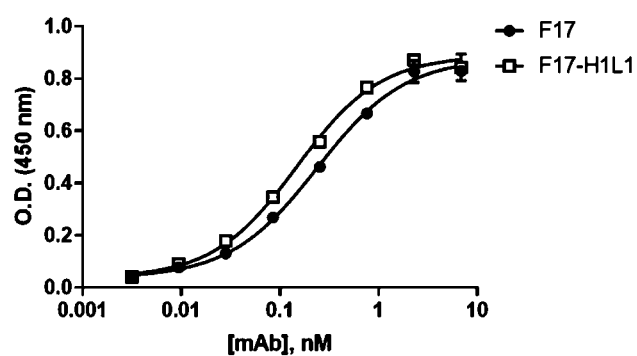
FIGS. 6A-6B show the results for the dose-dependent binding of the humanized F17 mAbs to immobilized FOLR1 extracellular domain in an ELISA assay.
Figure 6B:
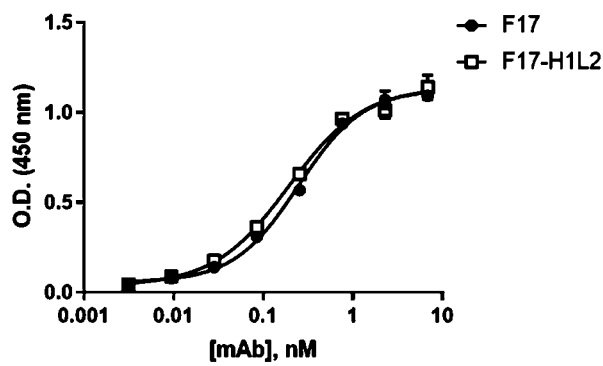
Figure 7A:
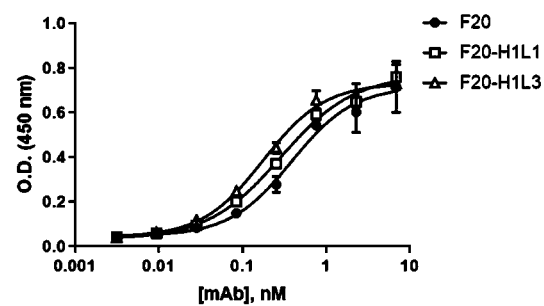
FIGS. 7A-7D show the results for the dose-dependent binding of the humanized F20 mAbs to immobilized FOLR1 extracellular domain in an ELISA assay.
Figure 7B:
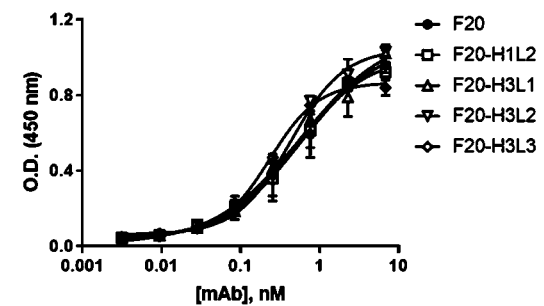
Figure 7C:
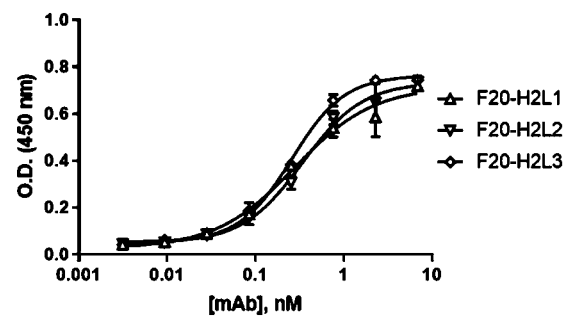
Figure 7D:
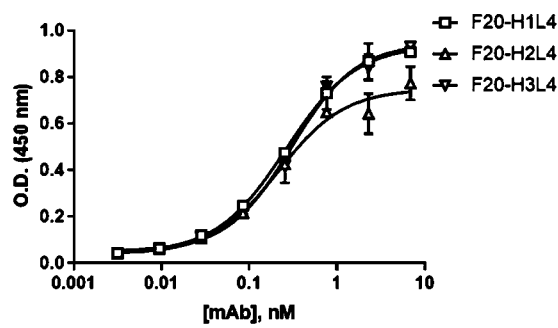
Figure 8A:
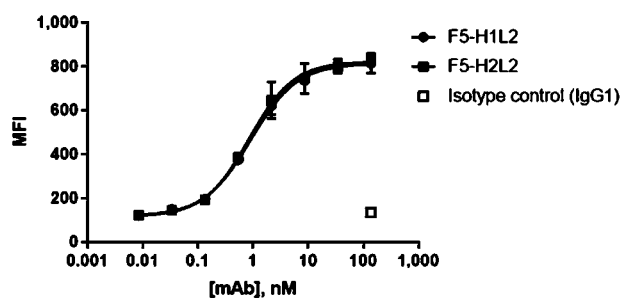
FIGS. 8A-8J show the results for the dose-dependent binding of the humanized mAbs to SK-OV-3 cells.
Figure 8B:
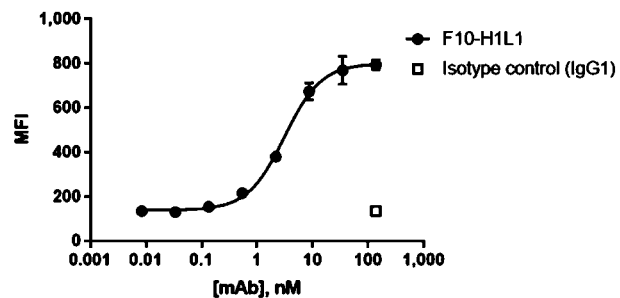
Figure 8C:
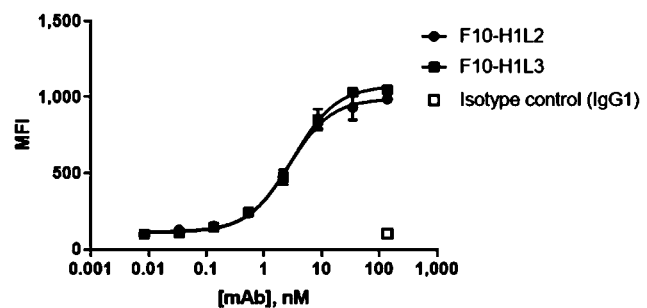
Figure 8D:
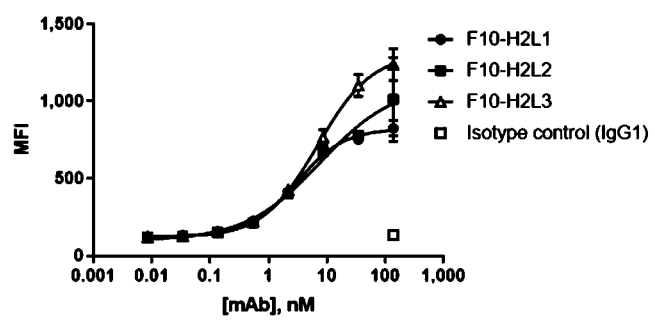
Figure 8E:
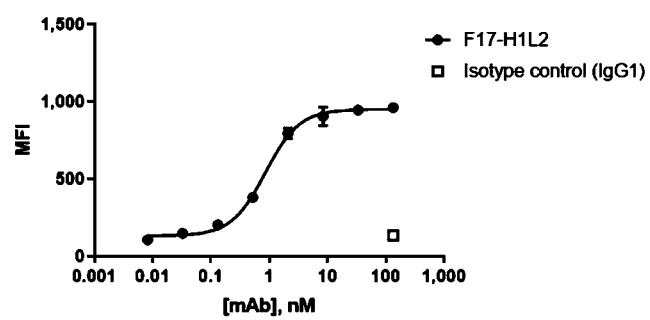
Figure 8F:
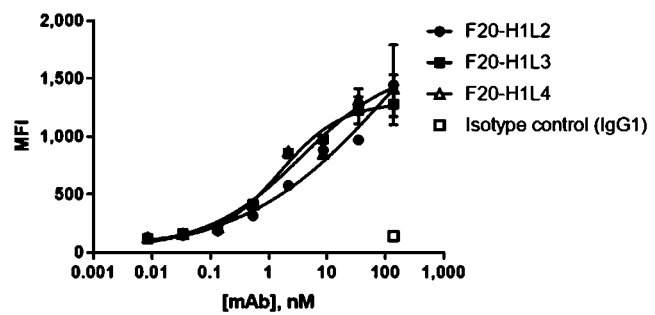
Figure 8G:
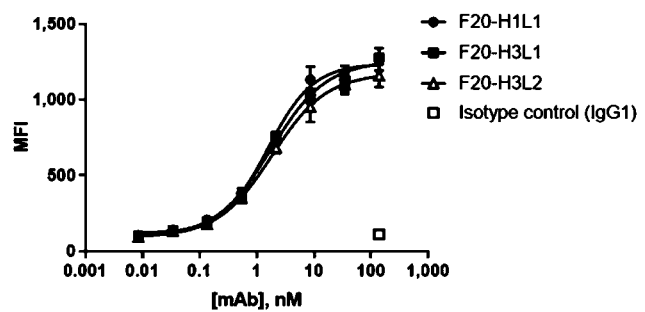
Figure 8H:
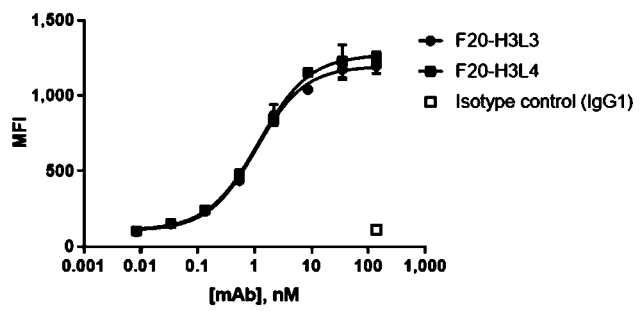
Figure 8I:
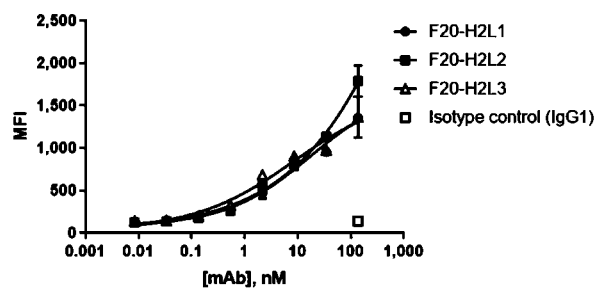
Figure 8J:
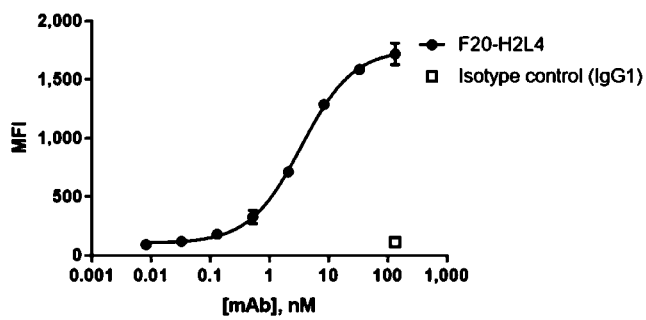

The mouse anti-FOLR1 mAbs were humanized to reduce the potential of immunogenicity when used in human patients. The sequences of the variable regions of the heavy and light chains (VH and VL) were compared with the human antibody sequences in the Protein Data Bank (PDB) database and homology models were built. The CDRs in both the heavy and light chains of the mouse mAbs were grafted into human frameworks that have the highest possibility of maintaining the proper structure likely required for antigen binding. Backmutations from human residues to mouse residue or other mutations were designed when necessary. The sequences of the humanized VH and VL regions are shown in Table 8. The humanized VH and VL regions were fused to the constant regions of human IgG1 heavy chain and kappa light chain, respectively. Constructs corresponding to the mAb sequences were used for transient transfection in CHO cells and purified mAbs were analyzed for their ability to bind to immobilized FOLR1 extracellular domain on ELISA. Isotype control was tested in the assays to confirm there is no non-specific binding above the assay background. The results for the humanized F5 clones are shown in FIG. 4A-4C; the results for the humanized F10 clones are shown in FIG. 5A-5B; the results for the humanized F17 clones are shown in FIG. 6A-6B; the results for the humanized F20 clones are shown in FIG. 7A-7D.

The humanized anti-FOLR1 mAbs were tested for their ability to bind to SK-OV-3 cells using FACS analysis. The data are shown in FIGS. 8A-8J.

Figure 9:
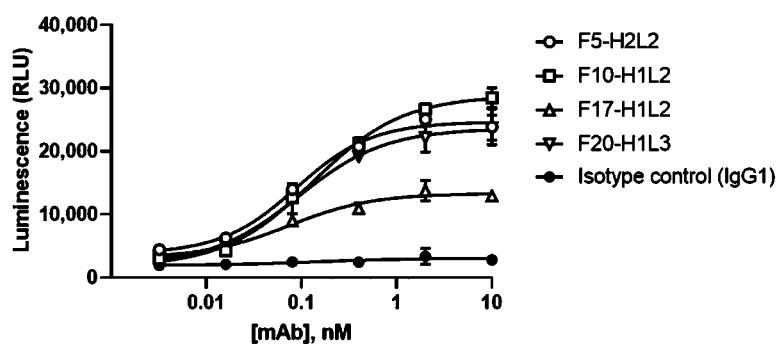
FIG. 9 shows the results for the antibody-dependent cellular cytotoxicity (ADCC) activity of four humanized anti-FOLR1 mAbs.

Antibody-dependent cellular cytotoxicity (ADCC) of mAbs was measured using the ADCC Reporter Bioassay Core Kit (Promega, cat. #G7010) according to the protocol provided by the manufacturer. Briefly, about 12,500 SK-OV-3 cells per well were mixed with various concentrations of testing antibodies in ADCC Assay Buffer in a half-area 96-well microplate (Corning-Costar, cat. #3696). Then, about 37,500 per well of ADCC Bioassay Effector cells were added to a final volume of 37.5 μL and mixed. The plate was incubated at 37° C. for 6 hours without shaking. To measure the luciferase activity, 12.5 μL of assay mix was removed from each well and 25 μL of the Bio-Glo Luciferase Assay Reagent was added. The plates were incubated at room temperature for 10 minutes with shaking. 30 μL per well of the mixture was transferred to a white plate (BRAND, cat. #781621) to measure luminescence on an EnVision 2102 multimode plate reader. The results for the ADCC activity of the 4 humanized mAbs are shown in FIG. 9. RLU, relative light unit.

TABLE 8

Sequences of heavy chain and light chain variable regions of humanized anti-FOLR1 mAbs

| VH/VL | SEQUENCE | ID: |
|---|---|---|
| F5-H1 | EVQLLESGGGLVQPGGSLRLSCAVSGFTFSNYGMSWVRQAPGKGLEWVATI SSGGSYTYYPDSVKGRFTISRDNSKNTLYLQMNSLRAEDTAVYYCSTQGSSG YVGYWGQGTLVTVSS | 113 |
| F5-H2 | EVQLVESGGGLVQPGGSLRLSCAVSGFTFSNYGMSWVRQAPGKGLEWVATI SSGGSYTYYPDSVKGRFTISRDNSKNTLYLQMNSLRAEDTAVYYCSTQGSSG YVGYWGQGTLVTVSS | 114 |
| F5-H3 | EVQLVESGGGLVQPGGSLRLSCAVSGFTFSNYGMSWVRQAPGKGLEWVATI SSGGSYTYYPDSVKGRFTISRDNSKNTLYLQMsSLRAEDTAVYYCSTQGSSG YVGYWGQGTLVTVSS | 115 |
| F5-H4 | EVQLVESGGGLVQPGGSLRLSCAVSGFTFSNYGMSWVRQAPGKGLEWVATI SSGGSYTYYPDSVKGRFTISRDNDKNTLYLQMsSLRAEDTAVYYCSTQGSSG YVGYWGQGTLVTVSS | 116 |
| F5-L1 | DIQMTQSPSSVSASVGDRVTITCKASQDITNFIGWYQHKPGKAPKLLISYTSIL ESGVPSRFSGSGSGRDYTLTISSLQPEDFATYYCLQYYNLWTFGGGTKVEIK | 117 |
| F5-L2 | DIQMTQSPSSVSASVGDRVTITCKASQDITNFIGWYQHKPGKAPKLLISYTSIL ESGVPSRFSGSGSGtDYTLTISSLQPEDFATYYCLQYYNLWTFGGGTKVEIK | 118 |
| F10-H1 | EVQLVQSGAEVKKPGSSVKVSCKASGYAFSSSWMNWVRQAPGQGLEWIGRI YPGDGYTHYNGMFKGRASLTADKSTSTGYMELSSLRSEDTAVFFCTRHGDFP YWYFDVVVGRGTLVTVSP | 119 |
| F10-H2 | EVQLVQSGAEVKKPGSSVKVSCKASGYAFSSSWMNWVRQAPGQGLEWIGRI YPGDGYTHYNGMFKGRASLTADKSTSTGYMELSSLRSEDTAVFFCTRHGDFP YWYFDVVVGRGTLVTVSS | 120 |
| F10-L1 | DIQMTQSPSTLSASVGDRVTITCRASENIDSYLAWYQQKPGRAPKLLVYAAT NLAVGVPSRFSGSGSGTEYTLTISSLQSDDFATYYCQHHYSTPPTFGQGTKLEI K | 121 |
| F10-L2 | DIQMTQSPSTLSASVGDRVTITCRASENIDSYLAWYQQKPGRAPKLLVYAAT NLAVGVPSRFSGSGSGTEYTLTISSLQpDDFATYYCQHHYSTPPTFGQGTKLEI K | 122 |
| F10-L3 | DIQMTQSPSTLSASVGDRVTITCRASENIDSYLAWYQQKPGRAPKLLVYAAT NLAVGVPSRFSGSGSGTEYTLTISSLQSeDFATYYCQHHYSTPPTFGQGTKLEI K | 123 |

TABLE 8-continued

Sequences of heavy chain and light chain variable
regions of humanized anti-FOLR1 mAbs

| VH/VL | SEQUENCE | ID: |
|---|---|---|
| F17-H1 | EVQLVETGGGLIQPGGSLRLSCAASGFTFSDFGMHWIRQAPGKGLEWVAYM SYTPGTFHYADTVKDRFTISRDNSKNTLYLQMNSLRAEDTAVYYCARVHVG TVDYWGQGTLVTVSS | 124 |
| F17-H2 | QVQLVESGGGVVQPGRSLRLSCAASGFTFSDFGMHWIRQAPGKGLEWVAY MSYTPGTFHYADTVKDRFTISRDNSKNTLYLQMNSLRAEDTAVYYCARVHV GTVDYWGQGTLVTVSS | 125 |
| F17-L1 | EVVLTQSPATLSLSPGERATLSCRASQNINNNLHWFQQKPGQAPRLLIKYASQ SISGIPARFSGSGSGTDFTLTISSLEPEDFAVYFCQQSNSWPALTFGQGTKVEIK | 126 |
| F17-L2 | EVVLTQSPATLSLSPGERATLSCRASQNINNNLHWFQQKPGQAPRLLIKYASQ SISGIPARFSGSGSGTDFTLTISSLEtEDFAVYFCQQSNSWPALTFGQGTKVEIK | 127 |
| F20-H1 | QVQLVQSGAEVKKPGSSVKVSCKASGYTFASYYLYWVRQAPGQGLEWIGEI NPRSGGTNFNEKFKSRATVTVDKSTSTAYMELSSLRSEDTAVYYCSRSGRLR GFYTMDYWGQGTLVTVSS | 128 |
| F20-H2 | QVQLVQSGAEVKKPGSSVKVSCKASGYTFASYYLYWVRQAPGQGLEWIGEI NPRSGGTNFNEKFKSRATVTVDaSTSTAYMELSSLRSEDTAVYYCSRSGRLRG FYTMDYWGQGTLVTVSS | 129 |
| F20-H3 | QVQLVQSGAEVKKPGSSVKVSCKASGYTFASYYLYWVRQAPGQGLEWIGEI NPRSGGTNFNEKFKSKATVTVDKSTNTAYMELSSLRSEDTAVYYCSRSGRLR GFYTMDYWGQGTLVTVSS | 130 |
| F20-L1 | DIVMTQSPDSLAVSLGERATINCKAGENVGSYVSWYQQKPGQPPKLLIYGAS NRYTGVPDRFSGSGSATDFTLTISSLQAEDVAVYYCGQTYRFLTFGQGTKVEI K | 131 |
| F20-L2 | DIVMTQSPDSLAVSLGERATINCKAGENVGSYVSWYQQKPGQsPKLLIYGAS NRYTGVPDRFSGSGSATDFTLTISSLQAEDVAVYYCGQTYRFLTFGQGTKVEI K | 132 |
| F20-L3 | DIQMTQSPSTLSASVGDRVTITCKAGENVGSYVSWYQQKPGKAPKLLIYGAS NRYTGVPARFSGSGSATEFTLTISSLQPDDFATYYCGQTYRFLTFGQGTKVEV K | 133 |
| F20-L4 | DIQMTQSPSTLSASVGDRVTITCKAGENVGSYVSWYQQKPGKAPKLLIYGAS NRYTGVPARFSGSGSATEFTLTISSLQPeDFATYYCGQTYRFLTFGQGTKVEV K | 134 |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

The invention claimed is:

1. An isolated monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequence of:
   (a) SEQ ID NOs: 29, 30, 31, 53, 54 and 55, respectively, or SEQ ID NOs: 77, 78, 79, 101, 102, and 103, respectively;
   (b) SEQ ID NOs: 20, 21, 22, 44, 45 and 46, respectively, or SEQ ID NOs: 68, 69, 70, 92, 93, and 94, respectively; or
   (c) SEQ ID NOs: 35, 36, 37, 59, 60 and 61, respectively, or SEQ ID NOs: 83, 84, 85, 107, 108, and 109, respectively;
wherein the antibody or antigen-binding fragment thereof specifically binds FOLR1.

2. The isolated monoclonal antibody or antigen-binding fragment thereof of claim 1, comprising a heavy chain variable region having a polypeptide sequence at least 95%, at least 96%, at least 97%, at least 98%, or at least 99% identical to SEQ ID NO: 120, 9, 3, 13, 113, 114, 115, 116, or 119, or a light chain variable region having a polypeptide sequence at least 95%, at least 96%, at least 97%, at least 98%, or at least 99% identical to SEQ ID NO: 122, 10, 4, 14, 117, 118, 121, or 123.

3. The isolated monoclonal antibody or antigen-binding fragment thereof of claim 1, comprising:
   (a) a heavy chain variable region having the polypeptide sequence of SEQ ID NO: 120, and a light chain variable region having the polypeptide sequence of SEQ ID NO: 122;
   (b) a heavy chain variable region having the polypeptide sequence of SEQ ID NO:9, and a light chain variable region having the polypeptide sequence of SEQ ID NO: 10;
   (c) a heavy chain variable region having the polypeptide sequence of SEQ ID NO:3, and a light chain variable region having the polypeptide sequence of SEQ ID NO:4;
   (d) a heavy chain variable region having the polypeptide sequence of SEQ ID NO: 13, and a light chain variable region having the polypeptide sequence of SEQ ID NO: 14;
   (e) a heavy chain variable region having the polypeptide sequence of SEQ ID NO: 113, and a light chain variable region having the polypeptide sequence of SEQ ID NO: 117;
   (f) a heavy chain variable region having the polypeptide sequence of SEQ ID NO: 113, and a light chain variable region having the polypeptide sequence of SEQ ID NO: 118;
   (g) a heavy chain variable region having the polypeptide sequence of SEQ ID NO: 114, and a light chain variable region having the polypeptide sequence of SEQ ID NO: 117;
   (h) a heavy chain variable region having the polypeptide sequence of SEQ ID NO:114, and a light chain variable region having the polypeptide sequence of SEQ ID NO:118;
   (i) a heavy chain variable region having the polypeptide sequence of SEQ ID NO:115, and a light chain variable region having the polypeptide sequence of SEQ ID NO:117;
   (j) a heavy chain variable region having the polypeptide sequence of SEQ ID NO:115, and a light chain variable region having the polypeptide sequence of SEQ ID NO:118;
   (k) a heavy chain variable region having the polypeptide sequence of SEQ ID NO:116, and a light chain variable region having the polypeptide sequence of SEQ ID NO:117;
   (l) a heavy chain variable region having the polypeptide sequence of SEQ ID NO:116, and a light chain variable region having the polypeptide sequence of SEQ ID NO:118;
   (m) a heavy chain variable region having the polypeptide sequence of SEQ ID NO:119, and a light chain variable region having the polypeptide sequence of SEQ ID NO:121;
   (n) a heavy chain variable region having the polypeptide sequence of SEQ ID NO:119, and a light chain variable region having the polypeptide sequence of SEQ ID NO:122;
   (o) a heavy chain variable region having the polypeptide sequence of SEQ ID NO:119, and a light chain variable region having the polypeptide sequence of SEQ ID NO:123;
   (p) a heavy chain variable region having the polypeptide sequence of SEQ ID NO:120, and a light chain variable region having the polypeptide sequence of SEQ ID NO:121; or
   (q) a heavy chain variable region having the polypeptide sequence of SEQ ID NO:120, and a light chain variable region having the polypeptide sequence of SEQ ID NO:123.

4. The isolated monoclonal antibody or antigen-binding fragment thereof of claim 1, wherein the antibody or antigen-binding fragment thereof is chimeric or humanized.

5. The isolated monoclonal antibody or antigen-binding fragment thereof of claim 1, wherein the monoclonal antibody or antigen-binding fragment thereof is capable of binding FOLR1 and inducing effector-mediated tumor cell lysis.

6. A pharmaceutical composition, comprising the isolated monoclonal antibody or antigen-binding fragment thereof of claim 1 and a pharmaceutically acceptable carrier.

7. A method of treating cancer or targeting FOLR1 on a cancer cell surface in a subject in need thereof, comprising administering to the subject the pharmaceutical composition of claim 6.

8. A method of producing a pharmaceutical composition comprising the monoclonal antibody or antigen-binding fragment of claim 1, comprising combining the monoclonal antibody or antigen-binding fragment thereof with a pharmaceutically acceptable carrier to obtain the pharmaceutical composition.

9. A method of determining a level of FOLR1 in a subject, the method comprising:
 (a) obtaining a sample from the subject;
 (b) contacting the sample with the isolated monoclonal antibody or antigen-binding fragment thereof of claim 1; and
 (c) determining a level of FOLR1 in the subject.

10. The method of claim 9, wherein the sample is a tissue sample or a blood sample.

11. The method of claim 10, wherein the tissue sample is a cancer tissue sample.

12. An isolated bi specific antibody or antigen-binding fragment thereof comprising the monoclonal antibody or antigen-binding fragment thereof of claim 1.

13. A pharmaceutical composition comprising the isolated bispecific antibody or antigen-binding fragment thereof of claim 12 and a pharmaceutically acceptable carrier.

* * * * *